United States Patent
Bell et al.

(10) Patent No.: US 8,754,096 B2
(45) Date of Patent: Jun. 17, 2014

(54) PIPERIDINONE CARBOXAMIDE AZAINDANE CGRP RECEPTOR ANTAGONISTS

(75) Inventors: Ian M. Bell, Harleysville, PA (US); Mark E. Fraley, North Wales, PA (US); Steven N. Gallicchio, Horsham, PA (US); Anthony Ginnetti, Perkasie, PA (US); Helen J. Mitchell, Richboro, PA (US); Daniel V. Paone, Lansdale, PA (US); Donnette D. Staas, Holland, PA (US); Heather E. Stevenson, Philadelphia, PA (US); Cheng Wang, Fort Washington, PA (US); C. Blair Zartman, Hatfield, PA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 252 days.

(21) Appl. No.: 13/293,166

(22) Filed: Nov. 10, 2011

(65) Prior Publication Data
US 2012/0122899 A1    May 17, 2012

Related U.S. Application Data

(60) Provisional application No. 61/413,077, filed on Nov. 12, 2010, provisional application No. 61/425,034, filed on Dec. 20, 2010.

(51) Int. Cl.
*A61K 31/4545* (2006.01)
*A61K 31/527* (2006.01)
*A61P 25/06* (2006.01)
*C07D 471/20* (2006.01)

(52) U.S. Cl.
USPC ............ 514/278; 514/265.1; 546/15; 544/230

(58) Field of Classification Search
CPC . A61K 31/527; A61K 31/4545; C07D 471/20
USPC ................ 514/265.1, 278; 544/230; 546/15
See application file for complete search history.

(56) References Cited

FOREIGN PATENT DOCUMENTS

| WO | WO2004/082602 | 9/2004 |
|----|---------------|--------|
| WO | WO2004/092166 | 10/2004 |
| WO | WO2006/031610 | 2/2006 |
| WO | WO2006/031606 | 3/2006 |
| WO | WO2008/153849 | 12/2008 |
| WO | WO2009/065922 | 5/2009 |
| WO | WO2010/139717 | 12/2010 |

OTHER PUBLICATIONS

Written Opinon of the International Search Report for PCT/US2011/060081; 4 pages.
Ho, et. al.; The Lancet, (2008), "Efficacy and Tolerability of MK-097(telcagepant), a new oral antagonist of cacitonin gene-related peptide receptor, compared with zolmitriptan for acute migraine: a randomised, placebo-controlled parallel-treatment trial", vol. 372, pp. 2115-2123.
Connor, et. al.; Neurology,(2009), "Randomized, controlled trial of telcagepant for the acute treatment of migraine", vol. 73, pp. 970-977.
Shaw, et. al.; Bioorg. Med. Chem Lett; (2007), "Caprolactams as potent CGRP Receptor Antagonists for the treatment of migraine", vol. 17, pp. 4795-4798.
Copending U.S. Appl. No. 13/293,177, filed on Nov. 10, 2011, Merck, Sharp & Dohme Corp.
Copending U.S. Appl. No. 13/293,186, filed on Nov. 10, 2011, Merck, Sharp & Dohme Corp.

*Primary Examiner* — Kendra D Carter
*Assistant Examiner* — Jason A Deck
(74) *Attorney, Agent, or Firm* — John C. Todaro; H. Eric Fischer

(57) ABSTRACT

The present invention is directed to piperidinone carboxamide azaindane derivatives which are antagonists of CGRP receptors and useful in the treatment or prevention of diseases in which the CGRP is involved, such as migraine. The invention is also directed to pharmaceutical compositions comprising these compounds and the use of these compounds and compositions in the prevention or treatment of such diseases in which CGRP is involved.

35 Claims, No Drawings

PIPERIDINONE CARBOXAMIDE AZAINDANE CGRP RECEPTOR ANTAGONISTS

BACKGROUND OF THE INVENTION

CGRP (Calcitonin Gene-Related Peptide) is a naturally occurring 37-amino acid peptide that is generated by tissue-specific alternate processing of calcitonin messenger RNA and is widely distributed in the central and peripheral nervous system. CGRP is localized predominantly in sensory afferent and central neurons and mediates several biological actions, including vasodilation. CGRP is expressed in alpha- and beta-forms that vary by one and three amino acids in the rat and human, respectively. CGRP-alpha and CGRP-beta display similar biological properties. When released from the cell, CGRP initiates its biological responses by binding to the CGRP receptor which is a heterodimer consisting of the G-protein coupled calcitonin-like receptor (CLR) in association with the single transmembrane protein known as receptor activity modifying protein 1 ($RAMP_1$). CGRP receptors are predominantly coupled to the activation of adenylyl cyclase and have been identified and pharmacologically evaluated in several tissues and cells, including those of brain, cardiovascular, endothelial, and smooth muscle origin.

CGRP is a potent neuromodulator that has been implicated in the pathology of cerebrovascular disorders such as migraine and cluster headache. In clinical studies, elevated levels of CGRP in the jugular vein were found to occur during migraine attacks (Goadsby et al. (1990) *Ann. Neurol.* 28, 183-187), salivary levels of CGRP are elevated in migraine subjects between (Bellamy et al. (2006) *Headache* 46, 24-33) and during attacks (Cady et al. (2009) *Headache* 49, 1258-1266), and CGRP itself has been shown to trigger migrainous headache (Lassen et al. (2002) *Cephalalgia* 22, 54-61). In clinical trials, the CGRP receptor antagonist BIBN4096BS has been shown to be effective in treating acute attacks of migraine (Olesen et al. (2004) *New Engl. J. Med.* 350, 1104-1110) and was able to prevent headache induced by CGRP infusion in a control group (Petersen et al. (2005) *Clin. Pharmacol. Ther.* 77, 202-213). The orally bioavailable CGRP receptor antagonist telcagepant has also shown antimigraine effectiveness in phase III clinical trials (Ho et al. (2008) *Lancet* 372, 2115-2123; Connor et al. (2009) *Neurology* 73, 970-977).

CGRP-mediated activation of the trigeminovascular system may play a key role in migraine pathogenesis. Additionally, CGRP activates receptors on the smooth muscle of intracranial vessels, leading to increased vasodilation, which is thought to contribute to headache pain during migraine attacks (Lance, Headache Pathogenesis: Monoamines, Neuropeptides, Purines and Nitric Oxide, Lippincott-Raven Publishers, 1997, 3-9). The middle meningeal artery, the principle artery in the dura mater, is innervated by sensory fibers from the trigeminal ganglion which contain several neuropeptides, including CGRP. Trigeminal ganglion stimulation in the cat resulted in increased levels of CGRP, and in humans, activation of the trigeminal system caused facial flushing and increased levels of CGRP in the external jugular vein (Goadsby et al. (1988) *Ann. Neurol.* 23, 193-196). Electrical stimulation of the dura mater in rats increased the diameter of the middle meningeal artery, an effect that was blocked by prior administration of CGRP(8-37), a peptide CGRP receptor antagonist (Williamson et al. (1997) *Cephalalgia* 17, 525-531). Trigeminal ganglion stimulation increased facial blood flow in the rat, which was inhibited by CGRP(8-37) (Escott et al. (1995) *Brain Res.* 669, 93-99). Electrical stimulation of the trigeminal ganglion in marmoset produced an increase in facial blood flow that could be blocked by the non-peptide CGRP receptor antagonist BIBN4096BS (Doods et al. (2000) *Br. J. Pharmacol.* 129, 420-423). Thus the vascular effects of CGRP may be attenuated, prevented or reversed by a CGRP receptor antagonist.

CGRP-mediated vasodilation of rat middle meningeal artery was shown to sensitize neurons of the trigeminal nucleus caudalis (Williamson et al., The CGRP Family: Calcitonin Gene-Related Peptide (CGRP), Amylin, and Adrenomedullin, Landes Bioscience, 2000, 245-247). Similarly, distention of dural blood vessels during migraine headache may sensitize trigeminal neurons. Some of the associated symptoms of migraine, including extra-cranial pain and facial allodynia, may be the result of sensitized trigeminal neurons (Burstein et al. (2000) *Ann. Neurol.* 47, 614-624). A CGRP antagonist may be beneficial in attenuating, preventing or reversing the effects of neuronal sensitization.

The ability of the compounds of the present invention to act as CGRP receptor antagonists makes them useful pharmacological agents for disorders that involve CGRP in humans and animals, but particularly in humans. Such disorders include migraine and cluster headache (Doods (2001) *Curr. Opin. Invest. Drugs* 2, 1261-1268; Edvinsson et al. (1994) *Cephalalgia* 14, 320-327); chronic tension type headache (Ashina et al. (2000) *Neurology* 14, 1335-1340); pain (Yu et al. (1998) *Eur. J. Pharmacol.* 347, 275-282); chronic pain (Hulsebosch et al. (2000) *Pain* 86, 163-175); neurogenic inflammation and inflammatory pain (Holzer (1988) *Neuroscience* 24, 739-768; Delay-Goyet et al. (1992) *Acta Physiol. Scanda.* 146, 537-538; Salmon et al. (2001) *Nature Neurosci.* 4, 357-358); eye pain (May et al. (2002) *Cephalalgia* 22, 195-196), tooth pain (Awawdeh et al. (2002) *Int. Endocrin. J.* 35, 30-36), non-insulin dependent diabetes mellitus (Molina et al. (1990) *Diabetes* 39, 260-265); vascular disorders; inflammation (Zhang et al. (2001) *Pain* 89, 265); arthritis, bronchial hyperreactivity, asthma, (Foster et al. (1992) *Ann. NY Acad. Sci.* 657, 397-404; Schini et al. (1994) *Am. J. Physiol.* 267, H2483-H2490; Zheng et al. (1993) *J. Virol.* 67, 5786-5791); shock, sepsis (Beer et al. (2002) *Crit. Care Med.* 30, 1794-1798); opiate withdrawal syndrome (Salmon et al. (2001) *Nature Neurosci.* 4, 357-358); morphine tolerance (Menard et al. (1996) *J. Neurosci.* 16, 2342-2351); hot flashes in men and women (Chen et al. (1993) *Lancet* 342, 49; Spetz et al. (2001) *J. Urology* 166, 1720-1723); allergic dermatitis (Wallengren (2000) *Contact Dermatitis* 43, 137-143); psoriasis; encephalitis, brain trauma, ischaemia, stroke, epilepsy, and neurodegenerative diseases (Rohrenbeck et al. (1999) *Neurobiol. Dis.* 6, 15-34); skin diseases (Geppetti and Holzer, Eds., Neurogenic Inflammation, 1996, CRC Press, Boca Raton, Fla.), neurogenic cutaneous redness, skin rosaceousness and erythema; tinnitus (Herzog et al. (2002) *J. Membr. Biol.* 189, 225); obesity (Walker et al. (2010) *Endocrinology* 151, 4257-4269); inflammatory bowel disease, irritable bowel syndrome, (Hoffman et al. (2002) *Scand. J. Gastroenterol.* 37, 414-422) and cystitis. Of particular importance is the acute or prophylactic treatment of headache, including migraine and cluster headache.

U.S. Pat. No. 7,390,798, granted Jun. 24, 2008 and U.S. Patent Publication No.: US 2010/0179166, published Jul. 15, 2010, disclose carboxamide CGRP receptor antagonist. The present invention is directed to a class of highly potent CGRP receptor antagonists as compared to earlier disclosed analogues, pharmaceutical compositions comprising them and their use in therapy.

SUMMARY OF THE INVENTION

The present invention is directed to piperidinone carboxamide azaindane derivatives which are highly potent antagonists of CGRP receptors and useful in the treatment or prevention of diseases in which the CGRP is involved, such as migraine. The invention is also directed to pharmaceutical compositions comprising these compounds and the use of these compounds and compositions in the prevention or treatment of such diseases in which CGRP is involved.

DETAILED DESCRIPTION OF THE INVENTION

The present invention is directed to a genus of compounds of Formula I:

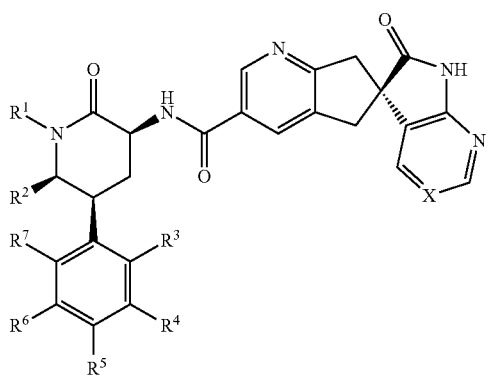

I or a pharmaceutically acceptable salt thereof, wherein:
X is selected from —C($R^8$)═ or —N═, wherein $R^8$ is hydrogen, F or CN;
$R^1$ is selected from the group consisting of: $C_{1-4}$alkyl, cyclopropylmethyl, cyclobutylmethyl and [1-(trifluoromethyl)cyclopropyl]methyl, each of which is optionally substituted with one or more substituents as allowed by valence independently selected from the group consisting of: F and hydroxy;
$R^2$ is selected from hydrogen and methyl;
when $R^2$ is hydrogen then
  $R^3$ is selected from hydrogen, F or Cl;
  $R^4$ is selected from hydrogen, F or Cl;
  $R^5$ is hydrogen;
  $R^6$ is selected from hydrogen or F; and
  $R^7$ is selected from hydrogen, F or Cl;
  except that at least two of $R^3$, $R^4$, $R^6$ and $R^7$ must be F or Cl unless $R^3$ is F in which case $R^4$, $R^6$ and $R^7$ may all be hydrogen; and if $R^4$ is Cl then $R^7$ cannot be Cl;
when $R^2$ is methyl then
  $R^3$ is selected from hydrogen, methyl, F, Cl, or Br;
  $R^4$ is selected from hydrogen, methyl, F or Cl;
  $R^5$ is selected from hydrogen or F;
  $R^6$ is selected from hydrogen or F; and
  $R^7$ is selected from hydrogen, methyl, F or Cl;
  except that if $R^5$ is F then at least three of $R^3$, $R^4$, $R^6$ and $R^7$ must be F; and if $R^4$ is methyl or Cl then $R^7$ cannot be methyl or Cl.

Within the genus, the invention encompasses a first sub-genus of compounds of Formula I, or a pharmaceutically acceptable salt thereof, wherein X is —N═.

Also within the genus, the invention encompasses a second sub-genus of compounds of Formula I, or a pharmaceutically acceptable salt thereof, wherein X is —CH═.

Also within the genus, the invention encompasses a third sub-genus of compounds of Formula I, or a pharmaceutically acceptable salt thereof, wherein X is —C(CN)═.

Also within the genus, the invention encompasses a fourth sub-genus of compounds of Formula I, or a pharmaceutically acceptable salt thereof, wherein $R^1$ is $C_{1-4}$alkyl, optionally substituted with 1 to 3 F or hydroxy, or both.

Within the fourth sub-genus, the invention encompasses a first class of compounds of Formula I, or a pharmaceutically acceptable salt thereof, wherein $R^1$ is selected from: isopropyl, 2,2,2-trifluoroethyl, 2,2-difluoroethyl, 2-methylpropyl, 3,3,3-trifluoropropyl and 3,3,3-trifluoro-2-hydroxypropyl.

Within the first class, the invention encompasses a first sub-class of compounds of Formula I, or a pharmaceutically acceptable salt thereof, wherein $R^1$ is 2,2,2-trifluoroethyl.

Also within the genus, the invention encompasses a fifth sub-genus of compounds of Formula I, or a pharmaceutically acceptable salt thereof, wherein $R^2$ is hydrogen.

Within the fifth sub-genus, the invention encompasses a second class of compounds of Formula I, or a pharmaceutically acceptable salt thereof, wherein at least two of $R^3$, $R^4$, $R^6$ and $R^7$ are F or Cl, except that if $R^4$ is Cl then $R^7$ cannot be Cl.

Also within the fifth sub-genus, the invention encompasses a third class of compounds of Formula I, or a pharmaceutically acceptable salt thereof, wherein $R^3$ is F and $R^4$, $R^6$ and $R^7$ are hydrogen.

Also within the genus, the invention encompasses a sixth sub-genus of compounds of Formula I, or a pharmaceutically acceptable salt thereof, wherein $R^2$ is methyl.

Within the sixth sub-genus, the invention encompasses a fourth class of compounds of Formula I, or a pharmaceutically acceptable salt thereof, wherein $R^5$ is F and at least three of $R^3$, $R^4$, $R^6$ and $R^7$ are F.

Also within the sixth sub-genus, the invention encompasses a fifth class of compounds of Formula I, or a pharmaceutically acceptable salt thereof, wherein $R^5$ is hydrogen and if $R^4$ is methyl or Cl then $R^7$ cannot be methyl or Cl.

Also within the sixth sub-genus, the invention encompasses a sixth class of compounds of Formula I, or a pharmaceutically acceptable salt thereof, wherein $R^3$ is selected from hydrogen, methyl, F or Cl; $R^4$ is selected from hydrogen, methyl, F or Cl; $R^5$ is hydrogen; $R^6$ is selected from hydrogen or F; and $R^7$ is selected from hydrogen, methyl, F or Cl; except that if $R^4$ is methyl or Cl then $R^7$ cannot be methyl or Cl.

The invention also encompasses a compound selected from the following:

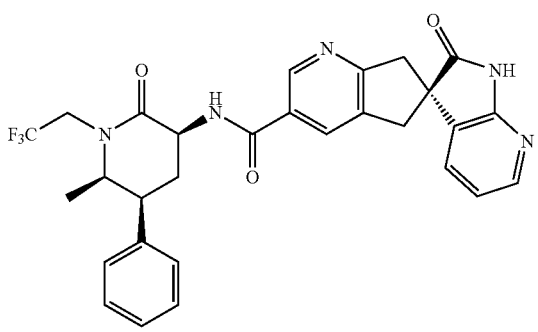

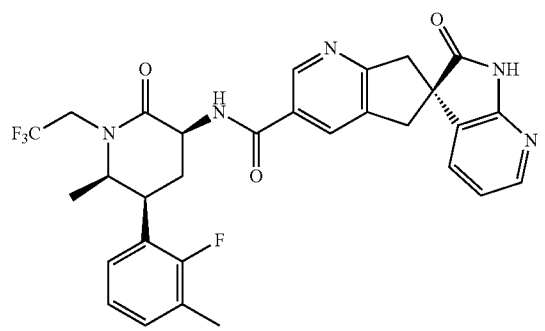
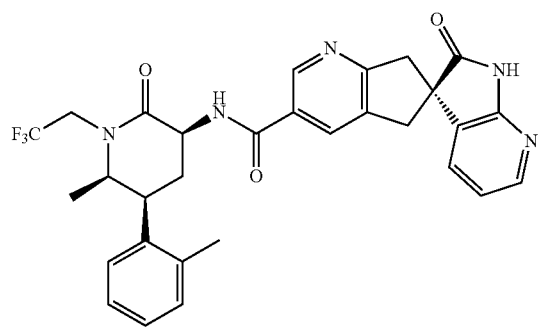
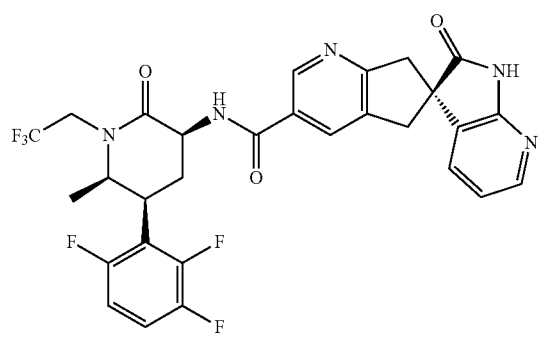
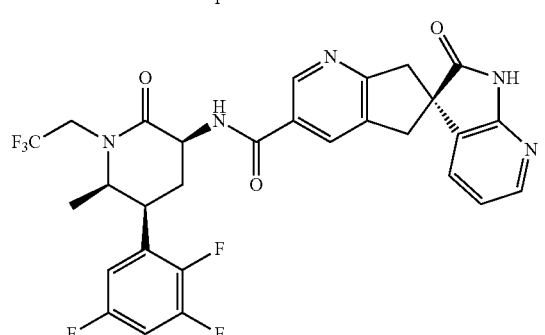
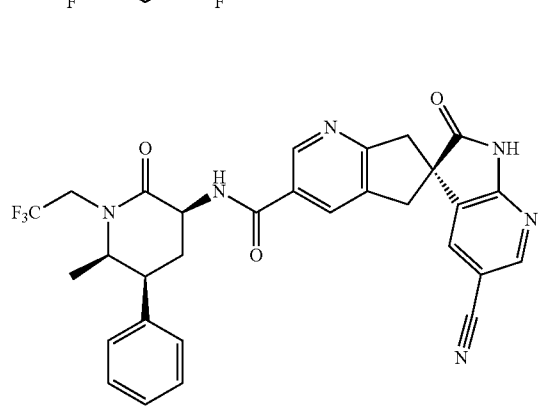
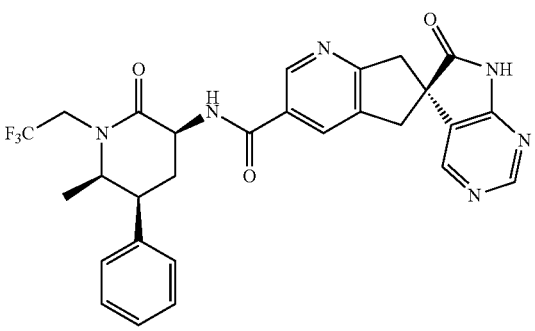
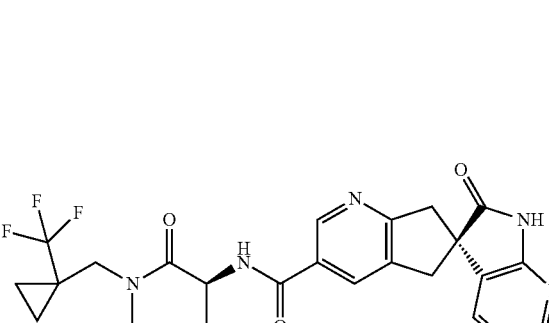
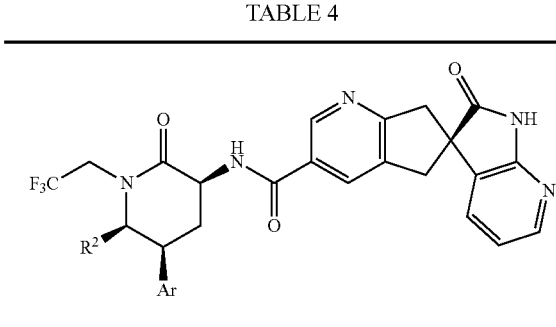
TABLE 4
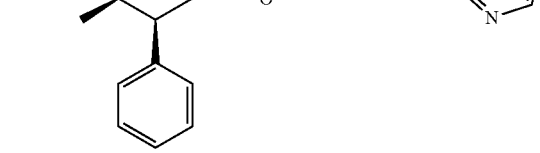
| R² | Ar |
|---|---|
| H | 2-fluorophenyl |
| Me | 2-chlorophenyl |
| Me | 3-methylphenyl |
| H | 2,3-difluorophenyl |
| H | 2,3,5-trifluorophenyl |
| H | 2-chloro-6-fluorophenyl |
| H | 2,6-dichlorophenyl |
| H | 2,3-dichlorophenyl |
| H | 2,3,6-trifluorophenyl |
| Me | 2,3,5,6-tetrafluorophenyl |
| Me | 3-fluoro-2-methylphenyl |

TABLE 5

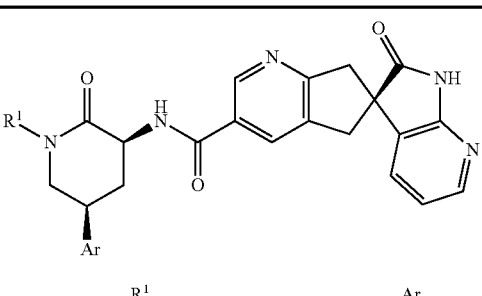

| R¹ | Ar |
| --- | --- |
| cyclobutylmethyl | 2,3-difluorophenyl |
| 2-methylpropyl | 2-fluorophenyl |
| cyclobutylmethyl | 2-fluorophenyl |
| isopropyl | 2-fluorophenyl |
| (2S)-3,3,3-trifluoro-2-hydroxypropyl | 2,3-difluorophenyl |

TABLE 6

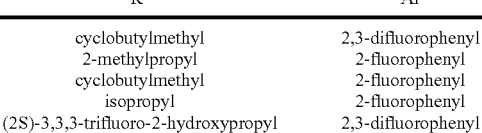

| R¹ |
| --- |
| 3,3,3-trifluoropropyl |
| 2-methylpropyl |
| (2S)-3,3,3-trifluoro-2-hydroxypropyl |
| cyclopropylmethyl |
| [1-(trifluoromethyl)cyclopropyl]methyl |
| 2,2-difluoroethyl |
| [(1R)-2,2-difluorocyclopropyl]methyl |
| [(1S)-2,2-difluorocyclopropyl]methyl | or a pharmaceutically acceptable salt thereof.

The invention also encompasses a pharmaceutical composition which comprises an inert carrier and the compound of Formula I, or a pharmaceutically acceptable salt thereof.

The invention also encompasses a method of treating headache in a mammalian patient in need of such treatment, which comprises administering to the patient a therapeutically effective amount of the compound of Formula I, or a pharmaceutically acceptable salt thereof. In a specific embodiment of the invention, the headache is migraine headache.

The invention also encompasses the use of a compound of Formula I, or a pharmaceutically acceptable salt thereof, and a pharmaceutically acceptable carrier, for the manufacture of a medicament for the treatment of headache. In a specific embodiment of the invention, the headache is migraine headache.

The invention is also directed to medicaments or pharmaceutical compositions for treating diseases or disorders in which CGRP is involved, such as migraine, which comprise a compound of Formula I, or a pharmaceutically acceptable salt thereof, and a pharmaceutically acceptable carrier.

The invention is also directed to the use of a compound of Formula I for treating diseases or disorders in which CGRP is involved, such as migraine.

The invention is further directed to a method for the manufacture of a medicament or a composition for treating diseases or disorders in which CGRP is involved, such as migraine, comprising combining a compound of Formula I with one or more pharmaceutically acceptable carriers.

The compounds of the present invention may contain one or more asymmetric centers and can thus occur as racemates and racemic mixtures, single enantiomers, diastereomeric mixtures and individual diastereomers. Additional asymmetric centers may be present depending upon the nature of the various substituents on the molecule. Each such asymmetric center will independently produce two optical isomers and it is intended that all of the possible optical isomers and diastereomers in mixtures and as pure or partially purified compounds are included within the ambit of this invention. Unless a specific stereochemistry is indicated, the present invention is meant to comprehend all such isomeric forms of these compounds.

The independent syntheses of these diastereomers or their chromatographic separations may be achieved as known in the art by appropriate modification of the methodology disclosed herein. Their absolute stereochemistry may be determined by the x-ray crystallography of crystalline products or crystalline intermediates which are derivatized, if necessary, with a reagent containing an asymmetric center of known absolute configuration.

If desired, racemic mixtures of the compounds may be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. The coupling reaction is often the formation of salts using an enantiomerically pure acid or base. The diasteromeric derivatives may then be converted to the pure enantiomers by cleavage of the added chiral residue. The racemic mixture of the compounds can also be separated directly by chromatographic methods utilizing chiral stationary phases, which methods are well known in the art.

Alternatively, any enantiomer of a compound may be obtained by stereoselective synthesis using optically pure starting materials or reagents of known configuration by methods well known in the art.

In the compounds of Formula I, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of generic Formula I. For example, different isotopic forms of hydrogen (H) include protium ($^1$H) and deuterium ($^2$H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds within generic Formula I can be prepared without undue experimentation by conventional techniques well known to those skilled in the art or by processes analogous to those described in the Schemes and Examples herein using appropriate isotopically-enriched reagents and/or intermediates.

Tautomers of compounds defined in Formula I are also included within the scope of the present invention. For example, compounds including carbonyl —CH$_2$C(O)— groups (keto forms) may undergo tautomerism to form hydroxyl —CH═C(OH)— groups (enol forms). Both keto and enol forms are included within the scope of the present invention.

As used herein, "alkyl" is intended to mean linear or branched structures having no carbon-to-carbon double or triple bonds. Thus, $C_{1-4}$alkyl is defined to identify the group as having 1, 2, 3 or 4 carbons in a linear or branched arrangement, such that $C_{1-4}$alkyl specifically includes, but is not limited to, methyl, ethyl, n-propyl, iso-propyl, n-butyl, iso-butyl and tert-butyl.

As is well understood by one having ordinary skill in the art, "F" means fluoro, "Cl" means chloro and "Br" means bromo.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives wherein the parent compound is modified by making acid or base salts thereof. Salts in the solid form may exist in more than one crystal structure, and may also be in the form of hydrates. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like. Salts derived from inorganic bases include aluminum, ammonium, calcium, copper, ferric, ferrous, lithium, magnesium, manganic salts, manganous, potassium, sodium, zinc, and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. In one aspect of the invention the salts are citric, hydrobromic, hydrochloric, maleic, phosphoric, sulfuric, fumaric, and tartaric acids. It will be understood that, as used herein, references to the compounds of Formula I are meant to also include the pharmaceutically acceptable salts.

Exemplifying the invention is the use of the compounds disclosed in the Examples and herein. Specific compounds within the present invention include a compound which may be selected from the group consisting of the compounds disclosed in the following Examples and pharmaceutically acceptable salts thereof and individual diastereomers thereof.

The subject compounds are useful in a method of antagonism of CGRP receptors in a patient such as a mammal in need of such antagonism comprising the administration of an effective amount of the compound. The present invention is directed to the use of the compounds disclosed herein as antagonists of CGRP receptors. In addition to primates, especially humans, a variety of other mammals can be treated according to the method of the present invention.

Another embodiment of the present invention is directed to a method for the treatment, control, amelioration, or reduction of risk of a disease or disorder in which the CGRP receptor is involved in a patient that comprises administering to the patient a therapeutically effective amount of a compound that is an antagonist of CGRP receptors.

The present invention is further directed to a method for the manufacture of a medicament for antagonism of CGRP receptors activity in humans and animals comprising combining a compound of the present invention with a pharmaceutical carrier or diluent.

The subject treated in the present methods is generally a mammal, for example a human being, male or female, in whom antagonism of CGRP receptor activity is desired. The term "therapeutically effective amount" means the amount of the subject compound that will elicit the biological or medical response of a tissue, system, animal or human that is being sought by the researcher, veterinarian, medical doctor or other clinician. As used herein, the term "treatment" refers both to the treatment and to the prevention or prophylactic therapy of the mentioned conditions, particularly in a patient who is predisposed to such disease or disorder.

The term "composition" as used herein is intended to encompass a product comprising the specified ingredients in the specified amounts, as well as any product which results, directly or indirectly, from combination of the specified ingredients in the specified amounts. Such term in relation to pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier. By "pharmaceutically acceptable" it is meant the carrier, diluent or excipient must be compatible with the other ingredients of the formulation and not deleterious to the recipient thereof.

The present invention includes within its scope prodrugs of the compounds of this invention. In general, such prodrugs will be functional derivatives of the compounds of this invention which are readily convertible in vivo into the required compound. Thus, in the methods of treatment of the present invention, the terms "administration of" or "administering a" compound shall encompass the treatment of the various conditions described with the compound specifically disclosed or with a compound which may not be specifically disclosed, but which converts to the specified compound in vivo after administration to the patient. Conventional procedures for the selection and preparation of suitable prodrug derivatives are described, for example, in "Design of Prodrugs," ed. H. Bundgaard, Elsevier, 1985. Metabolites of these compounds include active species produced upon introduction of compounds of this invention into the biological milieu.

The ability of the compounds of the present invention to act as CGRP receptor antagonists makes them useful pharmacological agents for disorders that involve CGRP in humans and animals, but particularly in humans.

The compounds of the present invention have utility in treating, preventing, ameliorating, controlling or reducing the risk of one or more of the following conditions or diseases: headache; migraine; cluster headache; chronic tension type headache; pain; chronic pain; neurogenic inflammation and inflammatory pain; neuropathic pain; eye pain; tooth pain; diabetes; non-insulin dependent diabetes mellitus; vascular disorders; inflammation; arthritis; bronchial hyperreactivity, asthma; shock; sepsis; opiate withdrawal syndrome; morphine tolerance; hot flashes in men and women; allergic dermatitis; psoriasis; encephalitis; brain trauma; epilepsy; neurodegenerative diseases; skin diseases; neurogenic cutaneous redness, skin rosaceousness and erythema; obesity; inflammatory bowel disease, irritable bowel syndrome, cystitis; and other conditions that may be treated or prevented by antagonism of CGRP receptors. Of particular importance is the acute or prophylactic treatment of headache, including migraine and cluster headache.

The subject compounds are further useful in a method for the prevention, treatment, control, amelioration, or reduction of risk of the diseases, disorders and conditions noted herein.

The subject compounds are further useful in a method for the prevention, treatment, control, amelioration, or reduction of risk of the aforementioned diseases, disorders and conditions in combination with other agents.

The compounds of the present invention may be used in combination with one or more other drugs in the treatment, prevention, control, amelioration, or reduction of risk of diseases or conditions for which compounds of Formula I or the other drugs may have utility, where the combination of the drugs together are safer or more effective than either drug alone. Such other drug(s) may be administered, by a route and in an amount commonly used therefor, contemporaneously or sequentially with a compound of Formula I. When a compound of Formula I is used contemporaneously with one or more other drugs, a pharmaceutical composition in unit dosage form containing such other drugs and the compound of Formula I is preferred. However, the combination therapy may also include therapies in which the compound of Formula I and one or more other drugs are administered on different overlapping schedules. It is also contemplated that when used in combination with one or more other active ingredients, the compounds of the present invention and the other active ingredients may be used in lower doses than when each is used singly. Accordingly, the pharmaceutical compositions of the present invention include those that contain one or more other active ingredients, in addition to a compound of Formula I.

For example, the present compounds may be used in conjunction with an anti-migraine agent, such as ergotamine and dihydroergotamine, or other serotonin agonists, especially a $5\text{-HT}_{1B/1D}$ agonist, for example sumatriptan, naratriptan, zolmitriptan, eletriptan, almotriptan, frovatriptan, donitriptan, and rizatriptan, a $5\text{-HT}_{1D}$ agonist such as PNU-142633 and a $5\text{-HT}_{1F}$ agonist such as LY334370; a cyclooxygenase inhibitor, such as a selective cyclooxygenase-2 inhibitor, for example rofecoxib, etoricoxib, celecoxib, valdecoxib or paracoxib; a non-steroidal anti-inflammatory agent or a cytokine-suppressing anti-inflammatory agent, for example with a compound such as ibuprofen, ketoprofen, fenoprofen, naproxen, indomethacin, sulindac, meloxicam, piroxicam, tenoxicam, lornoxicam, ketorolac, etodolac, mefenamic acid, meclofenamic acid, flufenamic acid, tolfenamic acid, diclofenac, oxaprozin, apazone, nimesulide, nabumetone, tenidap, etanercept, tolmetin, phenylbutazone, oxyphenbutazone, diflunisal, salsalate, olsalazine or sulfasalazine and the like; or glucocorticoids. Similarly, the instant compounds may be administered with an analgesic such as aspirin, acetaminophen, phenacetin, fentanyl, sufentanil, methadone, acetyl methadol, buprenorphine or morphine.

Additionally, the present compounds may be used in conjunction with an interleukin inhibitor, such as an interleukin-1 inhibitor; an NK-1 receptor antagonist, for example aprepitant; an NMDA antagonist; an NR2B antagonist; a bradykinin-1 receptor antagonist; an adenosine A1 receptor agonist; a sodium channel blocker, for example lamotrigine; an opiate agonist such as levomethadyl acetate or methadyl acetate; a lipoxygenase inhibitor, such as an inhibitor of 5-lipoxygenase; an alpha receptor antagonist, for example indoramin; an alpha receptor agonist; a vanilloid receptor antagonist; a renin inhibitor; a granzyme B inhibitor; a substance P antagonist; an endothelin antagonist; a norepinephrin precursor; anti-anxiety agents such as diazepam, alprazolam, chlordiazepoxide and chlorazepate; serotonin $5\text{HT}_2$ receptor antagonists; opiod agonists such as codeine, hydrocodone, tramadol, dextropropoxyphene and febtanyl; an mGluR5 agonist, antagonist or potentiator; a GABA A receptor modulator, for example acamprosate calcium; nicotinic antagonists or agonists including nicotine; muscarinic agonists or antagonists; a selective serotonin reuptake inhibitor, for example fluoxetine, paroxetine, sertraline, duloxetine, escitalopram, or citalopram; an antidepressant, for example amitriptyline, nortriptyline, clomipramine, imipramine, venlafaxine, doxepin, protriptyline, desipramine, trimipramine, or imipramine; a leukotriene antagonist, for example montelukast or zafirlukast; an inhibitor of nitric oxide or an inhibitor of the synthesis of nitric oxide.

Also, the present compounds may be used in conjunction with gap junction inhibitors; neuronal calcium channel blockers such as civamide; AMPA/KA antagonists such as LY293558; sigma receptor agonists; and vitamin B2.

Also, the present compounds may be used in conjunction with ergot alkaloids other than ergotamine and dihydroergotamine, for example ergonovine, ergonovine, methylergonovine, metergoline, ergoloid mesylates, dihydroergocornine, dihydroergocristine, dihydroergocryptine, dihydro-α-ergocryptine, dihydro-β-ergocryptine, ergotoxine, ergocornine, ergocristine, ergocryptine, α-ergocryptine, β-ergocryptine, ergosine, ergostane, bromocriptine, or methysergide.

Additionally, the present compounds may be used in conjunction with a beta-adrenergic antagonist such as timolol, propanolol, atenolol, metoprolol or nadolol, and the like; a MAO inhibitor, for example phenelzine; a calcium channel blocker, for example flunarizine, diltiazem, amlodipine, felodipine, nisolipine, isradipine, nimodipine, lomerizine, verapamil, nifedipine, or prochlorperazine; neuroleptics such as olanzapine, droperidol, prochlorperazine, chlorpromazine and quetiapine; an anticonvulsant such as topiramate, zonisamide, tonabersat, carabersat, levetiracetam, lamotrigine, tiagabine, gabapentin, pregabalin or divalproex sodium; an anti-hypertensive such as an angiotensin II antagonist, for example losartan, irbesartin, valsartan, eprosartan, telmisartan, olmesartan, medoxomil, candesartan and candesartan cilexetil, an angiotensin I antagonist, an angiotensin converting enzyme inhibitor such as lisinopril, enalapril, captopril, benazepril, quinapril, perindopril, ramipril and trandolapril; or botulinum toxin type A or B.

The present compounds may be used in conjunction with a potentiator such as caffeine, an H2-antagonist, simethicone, aluminum or magnesium hydroxide; a decongestant such as oxymetazoline, epinephrine, naphazoline, xylometazoline, propylhexedrine, or levo-desoxy-ephedrine; an antitussive such as caramiphen, carbetapentane, or dextromethorphan; a diuretic; a prokinetic agent such as metoclopramide or domperidone; a sedating or non-sedating antihistamine such as acrivastine, azatadine, bromodiphenhydramine, brompheniramine, carbinoxamine, chlorpheniramine, clemastine, dexbrompheniramine, dexchlorpheniramine, diphenhydramine, doxylamine, loratadine, phenindamine, pheniramine, phenyltoloxamine, promethazine, pyrilamine, terfenadine, triprolidine, phenylephrine, phenylpropanolamine, or pseudoephedrine. The present compounds also may be used in conjunction with anti-emetics.

In an embodiment of the invention the present compounds are used in conjunction with an anti-migraine agent, such as: ergotamine or dihydroergotamine; a 5-HT$_1$ agonist, especially a 5-HT$_{1B/1D}$ agonist, in particular, sumatriptan, naratriptan, zolmitriptan, eletriptan, almotriptan, frovatriptan, donitriptan, avitriptan and rizatriptan, and other serotonin agonists; and a cyclooxygenase inhibitor, such as a selective cyclooxygenase-2 inhibitor, in particular, rofecoxib, etoricoxib, celecoxib, valdecoxib or paracoxib.

The above combinations include combinations of a compound of the present invention not only with one other active compound, but also with two or more other active compounds. Likewise, compounds of the present invention may be used in combination with other drugs that are used in the prevention, treatment, control, amelioration, or reduction of risk of the diseases or conditions for which compounds of the present invention are useful. Such other drugs may be administered, by a route and in an amount commonly used therefore, contemporaneously or sequentially with a compound of the present invention. When a compound of the present invention is used contemporaneously with one or more other drugs, a pharmaceutical composition containing such other drugs in addition to the compound of the present invention is preferred. Accordingly, the pharmaceutical compositions of the present invention include those that also contain one or more other active ingredients, in addition to a compound of the present invention.

The weight ratio of the compound of the compound of the present invention to the other active ingredient(s) may be varied and will depend upon the effective dose of each ingredient. Generally, an effective dose of each will be used. Thus, for example, when a compound of the present invention is combined with another agent, the weight ratio of the compound of the present invention to the other agent will generally range from about 1000:1 to about 1:1000, or from about 200:1 to about 1:200. Combinations of a compound of the present invention and other active ingredients will generally also be within the aforementioned range, but in each case, an effective dose of each active ingredient should be used.

In such combinations the compound of the present invention and other active agents may be administered separately or in conjunction. In addition, the administration of one element may be prior to, concurrent to, or subsequent to the administration of other agent(s), and via the same or different routes of administration.

The compounds of the present invention may be administered by oral, parenteral (e.g., intramuscular, intraperitoneal, intravenous, ICV, intracisternal injection or infusion, subcutaneous injection, or implant), by inhalation spray, nasal, vaginal, rectal, sublingual, buccal or topical routes of administration and may be formulated, alone or together, in suitable dosage unit formulations containing conventional non-toxic pharmaceutically acceptable carriers, adjuvants and vehicles appropriate for each route of administration. In addition to the treatment of warm-blooded animals the compounds of the invention are effective for use in humans.

The pharmaceutical compositions for the administration of the compounds of this invention may conveniently be presented in dosage unit form and may be prepared by any of the methods well known in the art of pharmacy. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active compound is included in an amount sufficient to produce the desired effect upon the process or condition of diseases. As used herein, the term "composition" is intended to encompass a product comprising the specified ingredients in the specified amounts, as well as any product which results, directly or indirectly, from combination of the specified ingredients in the specified amounts.

The pharmaceutical compositions containing the active ingredient may be in a form suitable for oral use, for example, as tablets, troches, lozenges, aqueous or oily suspensions, dispersible powders or granules, emulsions, solutions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia; and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,166,452; and 4,265,874 to form osmotic therapeutic tablets for control release. Oral tablets may also be formulated for immediate release, such as fast melt tablets or wafers, rapid dissolve tablets or fast dissolve films.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example sodium carboxymethylcellulose, methylcellulose, hydroxy-propylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of the present invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions and the like, containing the compounds of the present invention are employed. Similarly, transdermal patches may also be used for topical administration.

The pharmaceutical composition and method of the present invention may further comprise other therapeutically active compounds as noted herein which are usually applied in the treatment of the above mentioned pathological conditions.

In the treatment, prevention, control, amelioration, or reduction of risk of conditions which require antagonism of CGRP receptor activity an appropriate dosage level will generally be about 0.01 to 500 mg per kg patient body weight per day which can be administered in single or multiple doses. A suitable dosage level may be about 0.01 to 250 mg/kg per day, about 0.05 to 100 mg/kg per day, or about 0.1 to 50 mg/kg per day. Within this range the dosage may be 0.05 to 0.5, 0.5 to 5 or 5 to 50 mg/kg per day. For oral administration, the compositions are may be provided in the form of tablets containing 1.0 to 1000 milligrams of the active ingredient, particularly 1.0, 5.0, 10.0, 15.0, 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient for the symptomatic adjustment of the dosage to the patient to be treated. The compounds may be administered on a regimen of 1 to 4 times per day, or may be administered once or twice per day.

When treating, preventing, controlling, ameliorating, or reducing the risk of headache, migraine, cluster headache, or other diseases for which compounds of the present invention are indicated, generally satisfactory results are obtained when the compounds of the present invention are administered at a daily dosage of from about 0.1 milligram to about 100 milligram per kilogram of animal body weight, given as a single daily dose or in divided doses two to six times a day, or in sustained release form. For most large mammals, the total daily dosage is from about 1.0 milligrams to about 1000 milligrams, or from about 1 milligrams to about 50 milligrams. In the case of a 70 kg adult human, the total daily dose will generally be from about 7 milligrams to about 350 milligrams. This dosage regimen may be adjusted to provide the optimal therapeutic response.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

The utility of the compounds in accordance with the present invention as antagonists of CGRP receptor activity may be demonstrated by methodology known in the art. Inhibition of the binding of $^{125}$I-CGRP to receptors and functional antagonism of CGRP receptors were determined as follows:

NATIVE RECEPTOR BINDING ASSAY: The binding of $^{125}$I-CGRP to receptors in SK-N-MC cell membranes was carried out essentially as described (Edvinsson et al. (2001) *Eur. J. Pharmacol.* 415, 39-44). Briefly, membranes (25 μg) were incubated in 1 mL of binding buffer [10 mM HEPES, pH 7.4, 5 mM MgCl$_2$ and 0.2% bovine serum albumin (BSA)] containing 10 μM $^{125}$I-CGRP and antagonist. After incubation at room temperature for 3 h, the assay was terminated by filtration through GFB glass fibre filter plates (PerkinElmer) that had been blocked with 0.5% polyethyleneimine for 3 h. The filters were washed three times with ice-cold assay buffer (10 mM HEPES, pH 7.4 and 5 mM MgCl$_2$), then the plates were air dried. Scintillation fluid (50 μL) was added and the radioactivity was counted on a Topcount (Packard Instrument). Data analysis was carried out by using Prism and the $K_i$ was determined by using the Cheng-Prusoff equation (Cheng & Prusoff (1973) *Biochem. Pharmacol.* 22, 3099-3108).

RECOMBINANT RECEPTOR: Human CL receptor (Genbank accession number L76380) was subcloned into the expression vector pIREShyg2 (BD Biosciences Clontech) as a 5'NheI and 3' PmeI fragment. Human RAMP1 (Genbank accession number AJ001014) was subcloned into the expression vector pIRESpuro2 (BD Biosciences Clontech) as a 5'NheI and 3'NotI fragment. HEK 293 cells (human embryonic kidney cells; ATCC # CRL-1573) were cultured in DMEM with 4.5 g/L glucose, 1 mM sodium pyruvate and 2 mM glutamine supplemented with 10% fetal bovine serum (FBS), 100 units/mL penicillin and 100 µg/mL streptomycin, and maintained at 37° C. and 95% humidity. Cells were subcultured by treatment with 0.25% trypsin with 0.1% EDTA in HBSS. Stable cell line generation was accomplished by co-transfecting 10 µg of DNA with 30 µg Lipofectamine 2000 (Invitrogen) in 75 cm² flasks. CL receptor and RAMP1 expression constructs were co-transfected in equal amounts. Twenty-four hours after transfection the cells were diluted and selective medium (growth medium+300 µg/mL hygromycin and 1 µg/mL puromycin) was added the following day. A clonal cell line was generated by single cell deposition utilizing a FACS Vantage SE (Becton Dickinson). Growth medium was adjusted to 150 µg/mL hygromycin and 0.5 µg/mL puromycin for cell propagation.

RECOMBINANT RECEPTOR BINDING ASSAY: Cells expressing recombinant human CL receptor/RAMP1 were washed with PBS and harvested in harvest buffer containing 50 mM HEPES, 1 mM EDTA and Complete™ protease inhibitors (Roche). The cell suspension was disrupted with a laboratory homogenizer and centrifuged at 48,000 g to isolate membranes. The pellets were resuspended in harvest buffer plus 250 mM sucrose and stored at −70° C. For binding assays, 20 µg of membranes were incubated in 1 mL binding buffer (10 mM HEPES, pH 7.4, 5 mM MgCl$_2$, and 0.2% BSA) for 3 h at room temperature containing 10 pM $^{125}$I-hCGRP (GE Healthcare) and antagonist. The assay was terminated by filtration through 96-well GFB glass fiber filter plates (PerkinElmer) that had been blocked with 0.05% polyethyleneimine. The filters were washed 3 times with ice-cold assay buffer (10 mM HEPES, pH 7.4, and 5 mM MgCl$_2$). Scintillation fluid was added and the plates were counted on a Topcount (Packard). Non-specific binding was determined and the data analysis was carried out with the apparent dissociation constant ($K_i$) determined by using a non-linear least squares fitting the bound CPM data to the equation below:

$$Y_{obsd} = \frac{(Y_{max} - Y_{min})(\% I_{max} - \%I_{min}/100) + Y_{min} + (Y_{max} - Y_{min})(100 - \%I_{max}/100)}{1 + ([Drug]/K_i(1 + [Radiolabel]/K_d)^{nH}}$$

Where Y is observed CPM bound, $Y_{max}$ is total bound counts, $Y_{min}$ is non specific bound counts, ($Y_{max}-Y_{min}$) is specific bound counts, % $I_{max}$ is the maximum percent inhibition, % I min is the minimum percent inhibition, radiolabel is the probe, and the $K_d$ is the apparent dissociation constant for the radioligand for the receptor as determined by hot saturation experiments.

RECOMBINANT RECEPTOR FUNCTIONAL ASSAY: Cells were resuspended in DMEM/F12 (Hyclone) supplemented with 1 g/L BSA and 300 µM isobutyl-methylxanthine. Cells were then plated in a 384-well plate (Proxiplate Plus 384; 509052761; Perkin-Elmer) at a density of 2,000 cells/well and incubated with antagonist for 30 min at 37° C. Human α-CGRP was then added to the cells at a final concentration of 1.2 nM and incubated an additional 20 min at 37° C. Following agonist stimulation, the cells were processed for cAMP determination using the two-step procedure according to the manufacturer's recommended protocol (HTRF cAMP dynamic 2 assay kit; 62AM4PEC; Cisbio). Raw data were transformed into concentration of cAMP using a standard curve then dose response curves were plotted and inflection point (IP) values were determined.

Examplary $K_i$ values in the recombinant receptor binding assay for exemplary compounds of the invention are provided in the table below:

| Example | $K_i$ (nM) |
|---|---|
| 1 | 0.067 |
| 3 | 0.067 |
| 4 | 0.015 |
| 5 | 0.017 |
| 6 | 0.21 |
| 11 | 0.25 |
| 17 | 0.055 |
| 26 | 0.093 |
| 30 | 0.14 |
| 31 | 0.17 |

CGRP binding data of analogues disclosed in U.S. Pat. No. 7,390,798 and US Publication No. 2010/0179166 are shown in the following table:

| Compound | $K_i$ (nM) |
|---|---|
| Example 8 from U.S. Pat. No. 7,390,798 | 7.4 |

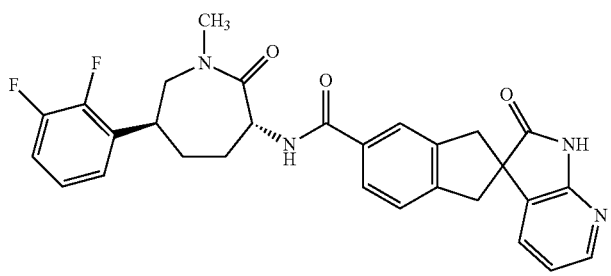 [SMILES: CN1C[C@H](c2cccc(F)c2F)CC[C@@H](NC(=O)c2ccc3c(c2)CC2(C3)C(=O)Nc3ncccc32)C1=O]

| Compound | $K_i$ (nM) |
|---|---|
| Example 9 from U.S. Pat. No. 7,390,798 | 1.9 |

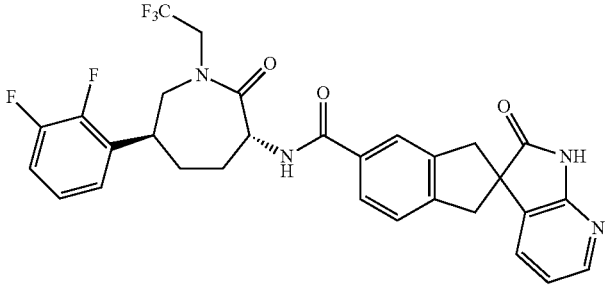 [SMILES: O=C(N[C@@H]1CC[C@@H](c2cccc(F)c2F)CN(CC(F)(F)F)C1=O)c1ccc2c(c1)CC1(C2)C(=O)Nc2ncccc21]

| Compound | $K_i$ (nM) |
|---|---|
| Example 10 from U.S. Pat. No. 7,390,798 | 1.7 |

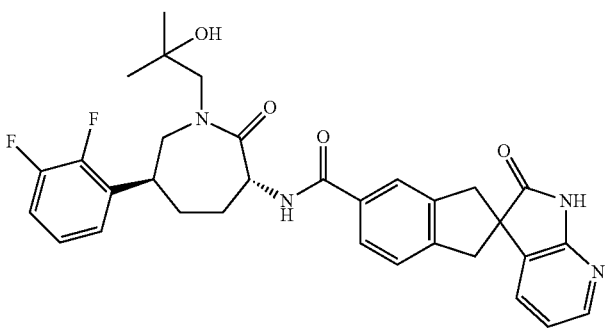 [SMILES: CC(C)(O)CN1C[C@H](c2cccc(F)c2F)CC[C@@H](NC(=O)c2ccc3c(c2)CC2(C3)C(=O)Nc3ncccc32)C1=O]

| Compound | $K_i$ (nM) |
|---|---|
| Example 8 from U.S. 2010/0179166 | 4.3 |

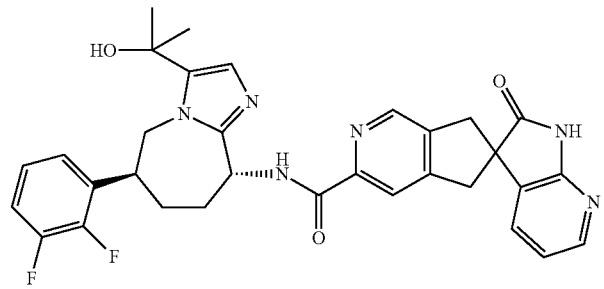 [SMILES: CC(C)(O)c1cnc2n1C[C@H](c1cccc(F)c1F)CC[C@H]2NC(=O)c1cc2c(cn1)CC1(C2)C(=O)Nc2ncccc21]

Example 32 from U.S. Pat. No. 7,390,798 possessed subnanomolar potency but is structurally distinct from the compounds of the invention described herein.

The following abbreviations are used throughout the text:
Me: methyl
Et: ethyl
t-Bu: tert-butyl
Bu: butyl
i-Pr: isopropyl
Ar: aryl
Ph: phenyl
Bn: benzyl
Py: pyridyl
Ac: acetylate
OAc: acetate
DCE: 1,2-dichloroethane
TFA: trifluoroacetic acid
TEA: triethylamine
Boc: tert-butoxycarbonyl
BOP: (Benzotriazol-1-yloxy)tris(dimethylamino)phosphonium hexafluorophosphate
DIEA: N,N-diisopropylethylamine
HOBT: 1-hydroxybenzotriazole
EDC: N-(3-dimethylaminopropyl)-N'-ethylcarbodiimide hydrochloride
PyClU: chlorodipyrrolidinocarbenium
n-BuLi: n-butyllithium
HATU: O-(7-azabenzotriazol-1-yl)-N,N,N'N'-tetramethyluronium hexafluorophosphate
EDTA: ethylenediaminetetraacetic acid
DMF: N,N-dimethylformamide
HMDS: hexamethyldisilazane
THF: tetrahydrofuran
DMSO: dimethylsulfoxide
SEM: 2-trimethylsilylethoxymethyl
SEMCl: 2-trimethylsilylethoxymethyl chloride
PBPB: pyridinium bromide perbromide
DMEM: Dulbecco's Modified Eagle Medium (High Glucose)
FBS: fetal bovine serum
BSA: bovine serum albumin
PBS: phosphate-buffered saline HEPES: N-(2-hydroxyethyl)piperazine-N'-(2-ethane-sulfonic acid)
min: minutes
h: hours
aq: aqueous
HPLC: high performance liquid chromatography
LCMS: liquid chromatography-mass spectrometry
SFC: supercritical fluid chromatography
NMP: 1-methyl-2-pyrrolidinone
DMA: N,N-dimethylacetamide
NBS: N-bromosuccinimide
dppf: 1,1'-bis(diphenylphosphino)ferrocene
dba: dibenzylideneacetone
Ms: methane sulfonyl
p-Ts: 4-toluenesulfonyl
trisyl: 2,4,6-triisopropylbenzenesulfonyl
DMAP: 4-(dimethylamino)pyridine Methods for preparing the compounds of this invention are illustrated in the following Schemes and Examples. Starting materials are made according to procedures known in the art or as illustrated herein.

The compounds of the present invention can be prepared readily according to the following Schemes and specific examples, or modifications thereof, using readily available starting materials, reagents and conventional synthesis procedures. In these reactions, it is also possible to make use of variants which are themselves known to those of ordinary skill in this art but are not mentioned in greater detail. The general procedures for making the compounds claimed in this invention can be readily understood and appreciated by one skilled in the art from viewing the following Schemes.

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. For example, effective dosages other than the particular dosages as set forth herein above may be applicable as a consequence of variations in the responsiveness of the mammal being treated for any of the indications with the compounds of the invention indicated above. Likewise, the specific pharmacological responses observed may vary according to and depending upon the particular active compounds selected or whether there are present pharmaceutical carriers, as well as the type of formulation and mode of administration employed, and such expected variations or differences in the results are contemplated in accordance with the objects and practices of the present invention. It is intended, therefore, that the invention be defined by the scope of the claims which follow and that such claims be interpreted as broadly as is reasonable.

Reaction Schemes

The compounds of the present invention can be prepared readily according to the following Schemes and specific examples, or modifications thereof, using readily available starting materials, reagents and conventional synthetic procedures. In these reactions, it is also possible to make use of variants which are themselves known to those of ordinary skill in this art but are not mentioned in greater detail. The general procedures for making the compounds claimed in this invention can be readily understood and appreciated by one skilled in the art from viewing the following Schemes.

Scheme 1 illustrates a route to 3-aminopiperidinone intermediates of type 1.5 which may be used to prepare compounds of the present invention. Aryl acetone 1.1 can be alkylated using the iodoalanine derivative 1.2 under basic conditions to provide keto ester 1.3. Reductive amination followed by cyclization and epimerization provides primarily cis-substituted lactam 1.4 as a racemic mixture. Chiral resolution using normal-phase liquid chromatography, for example, and removal of the Boc protecting group with HCl in EtOAc furnishes 3-aminopiperidinone 1.5 as a hydrochloride salt.

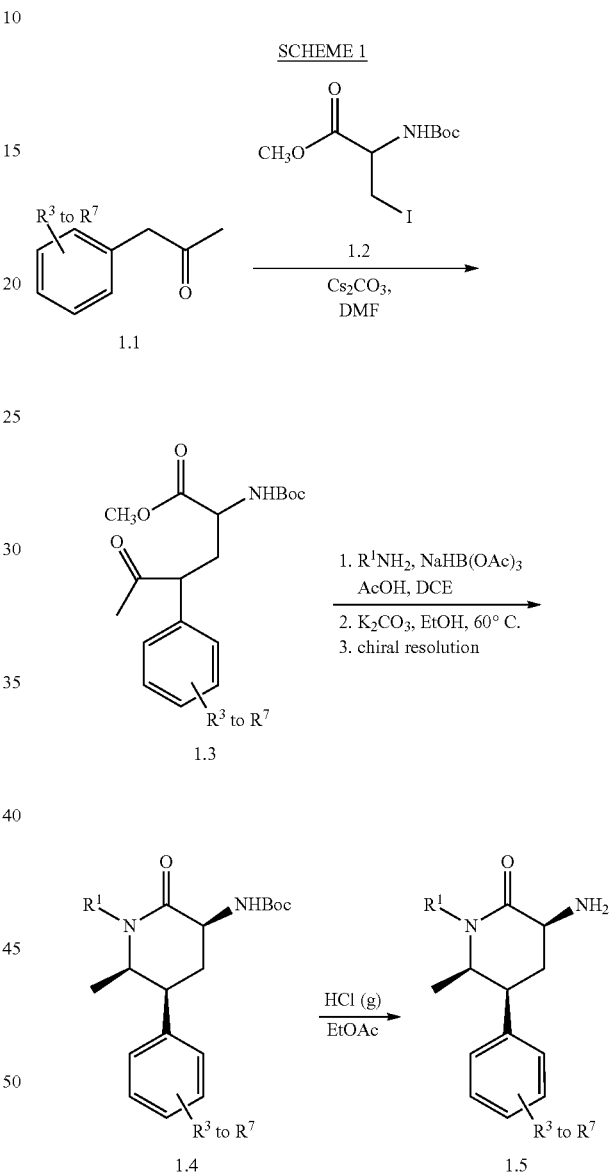

SCHEME 1

An alternative sequence to 3-aminopiperidinone intermediates of type 1.5 is shown in Scheme 2. Reductive amination of keto ester 1.3 with ammonia followed by epimerization provides 2.1 as a mostly cis-substituted racemic mixture. Chiral resolution of the enantiomers provides 2.2. N-Alkylation with LiHMDS as base, for example, and an alkyl halide or epoxide affords 2.3. Removal of the Boc protecting group with HCl then affords 1.5 as a hydrochloride salt.

SCHEME 2

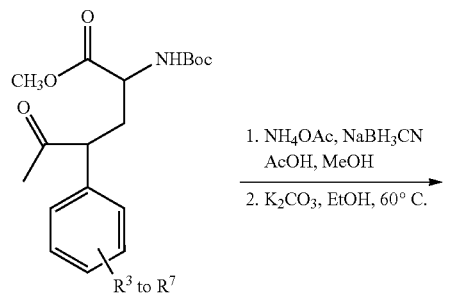
1.3

1. NH₄OAc, NaBH₃CN
   AcOH, MeOH
2. K₂CO₃, EtOH, 60° C.

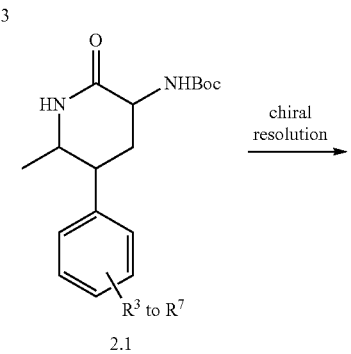
2.1 chiral resolution

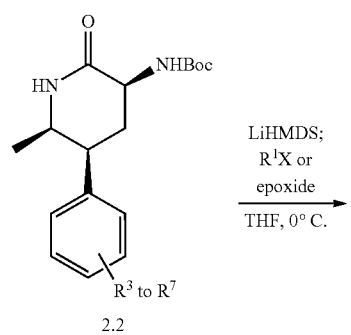
2.2

LiHMDS;
R¹X or epoxide
THF, 0° C.

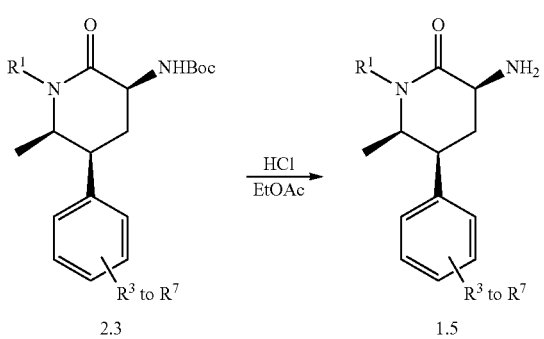
2.3     1.5

HCl
EtOAc

A third method to 3-aminopiperidinone intermediates of type 1.5 is shown in Scheme 3. N-Alkylation of 5-bromo-6-methylpyridin-2(1H)-one (3.1) using cesium carbonate as base and an alkyl halide followed by nitration provides 3.2. Palladium-catalyzed cross-coupling with an aryl boronic acid then affords 3.3. Hydrogenation using platinum oxide under acidic conditions and chiral resolution of the mostly cis-substituted racemic product mixture provides 1.5 as a single enantiomer.

SCHEME 3

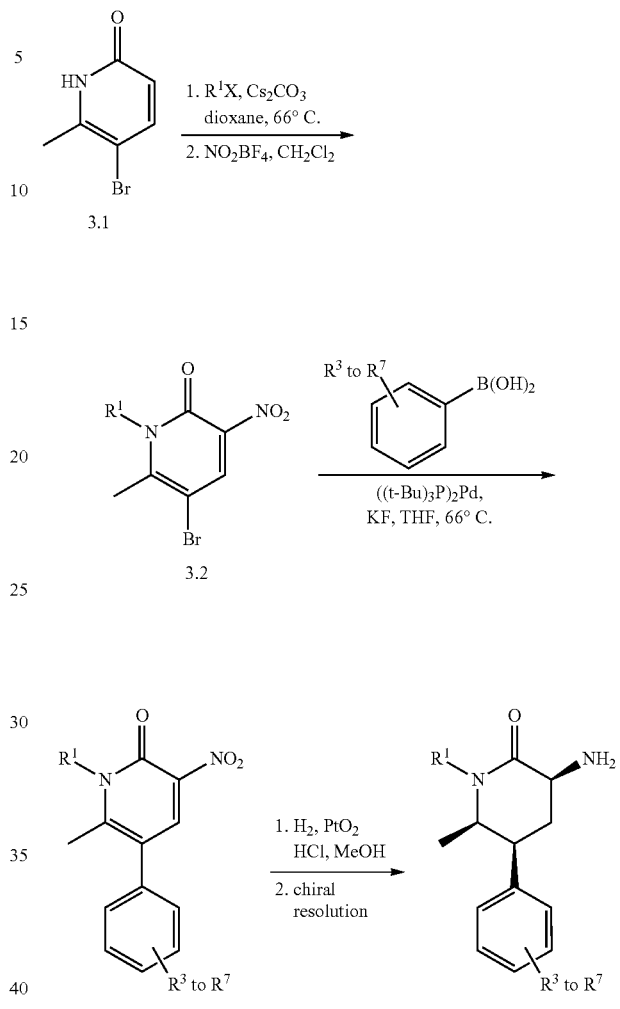

3.1

1. R¹X, Cs₂CO₃
   dioxane, 66° C.
2. NO₂BF₄, CH₂Cl₂

3.2

((t-Bu)₃P)₂Pd,
KF, THF, 66° C.

3.3

1. H₂, PtO₂
   HCl, MeOH
2. chiral resolution 1.5

A synthetic route to 3-aminopiperidinone intermediates of type 4.4 is shown in Scheme 4. Aryl acetonitrile 4.1 can be alkylated using the iodoalanine derivative 1.2 under basic conditions to provide cyano ester 4.2. Reductive cyclization using hydrogen and palladium hydroxide on carbon or Raney nickel, epimerization, and chiral resolution affords cis lactam 4.3 as a single enantiomer. N-Alkylation and removal of the Boc protecting group then provides 4.4 as a hydrochloride salt.

SCHEME 4

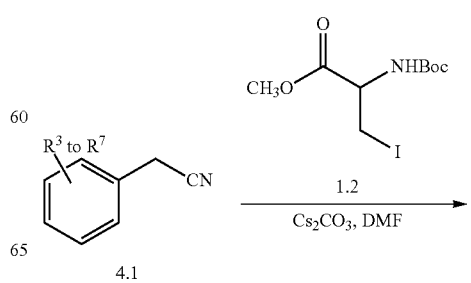

4.1

1.2

Cs₂CO₃, DMF

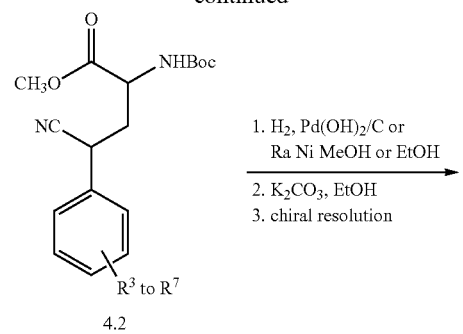

4.2

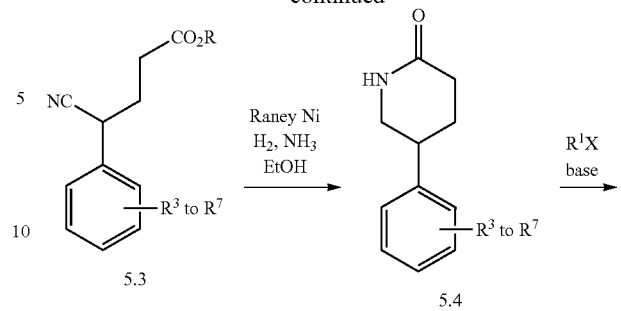

5.3 → 5.4

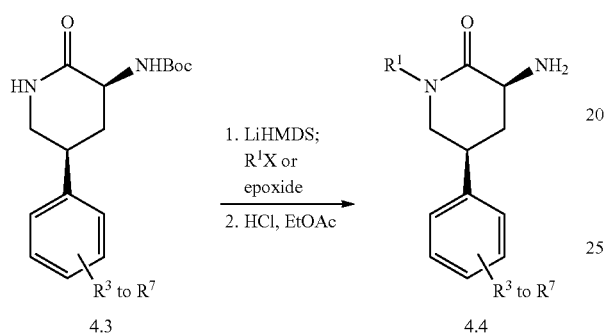

4.3 → 4.4

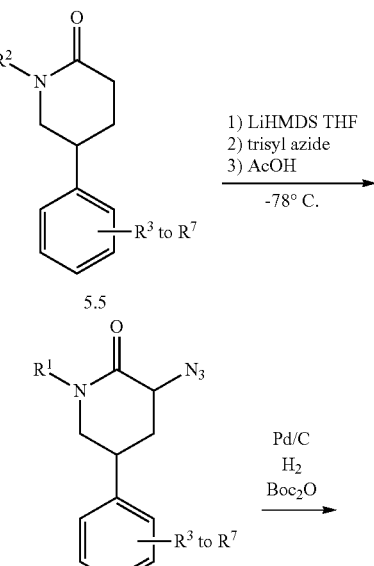

5.5 → 5.6 → 5.7

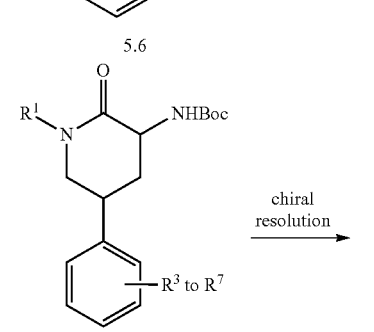

5.8 → 4.4

Scheme 5 illustrates an alternative route to 3-aminopiperidinone intermediates of type 4.4. The arylacetonitrile 5.1 may be condensed with acrylate 5.2 at elevated temperature to give the 4-cyanobutanoate ester 5.3. Hydrogenation of nitrile 5.3 using Raney nickel catalyst and an ethanolic solution of ammonia affords the corresponding amine product, which typically cyclizes in situ to provide piperidinone 5.4. N-Alkylation of lactam 5.4 may be accomplished by a variety of methods known to those skilled in the art of organic synthesis, the exact choice of conditions being influenced by the nature of the alkylating agent, R¹X. Electrophilic azidation of the resulting substituted lactam 5.5 can be accomplished using similar methodology to that described by Evans and coworkers (Evans et al. (1990) *J. Am. Chem. Soc.* 112, 4011-4030) to provide the azide 5.6 as a mixture of diastereoisomers, which can be separated by chromatography. The desired cis diastereomer of azide 5.6 may be reduced by catalytic hydrogenation in the presence of di-tert-butyl dicarbonate to give the corresponding Boc-protected amine 5.7, and separation of the enantiomers using chiral HPLC or SFC leads to the (3S,5S)-isomer 5.8. Finally, standard deprotection affords the desired 3-aminopiperidinone intermediate 4.4 as a hydrochloride salt.

SCHEME 5

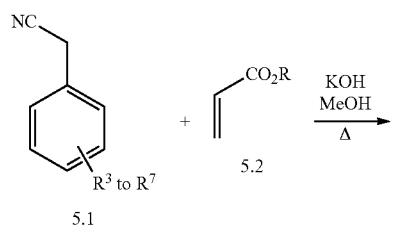

Another approach to 3-aminopiperidinone intermediates of interest, which is particularly useful for preparing 3-amino-6-methyl-5-arylpiperidin-2-ones such as 1.5, is outlined in Scheme 6. The pyridin-2(1H)-one 3.1 may be converted to the N-substituted pyridinone 6.1 by treatment with a suitable electrophile (R¹X) under basic conditions. Pyridinone 6.1 can then be subjected to Suzuki coupling with the boronic acid 6.2, and the resulting 5-arylpyridinone 6.3 may be hydrogenated using, for example, platinum(IV) oxide catalyst to afford the corresponding 5-arylpiperidinone 6.4, which is usually obtained as predominantly the cis isomer. Further elaboration of piperidinone 6.4 may be achieved using analogous methodology to that described in Scheme 5. Specifically, electrophilic azidation followed by one-pot reduction and Boc protection leads to carbamate 6.6, and the desired enantiomer may be obtained using chiral chromatography. In some cases, the desired diastereomer of azide 6.5 may be isolated as a racemic mixture of the (3S,5S,6R)- and (3R,5R,6S)-isomers following silica gel chromatography of the crude product, and this mixture may be elaborated as outlined in Scheme 6. In other cases, it may be advantageous to take a mixture of diastereomers of azide 6.5 forward to the corresponding carbamate 6.6. The mixture of carbamate 6.6 diastereomers may be epimerized under basic conditions, such as potassium carbonate in EtOH, to afford a mixture that is significantly enriched in the desired (3S,5S,6R)- and (3R,5R,6S)-isomers, further purification may be employed to obtain the enantiomer of interest as outlined herein.

A synthetic route to the azaoxindole pyridine acid intermediate 7.4 is shown in Scheme 7. Diazotization of aminopyridine 7.1, whose preparation is described in WO 2008/020902, followed by treatment with potassium iodide provides iodide 7.2. Palladium-catalyzed carbonylation in methanol then affords ester 7.3, which may be saponified with sodium hydroxide to furnish 7.4.

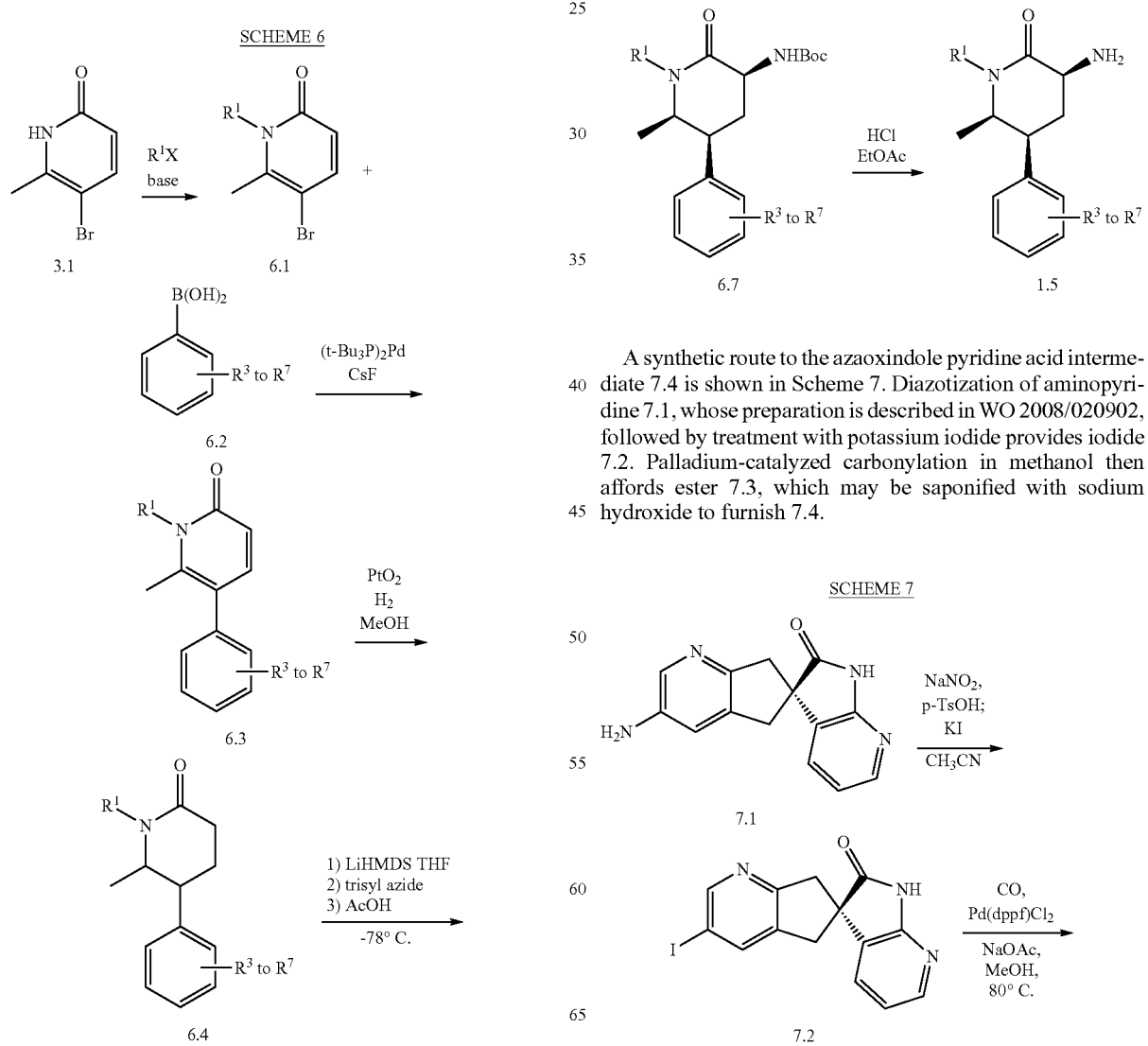

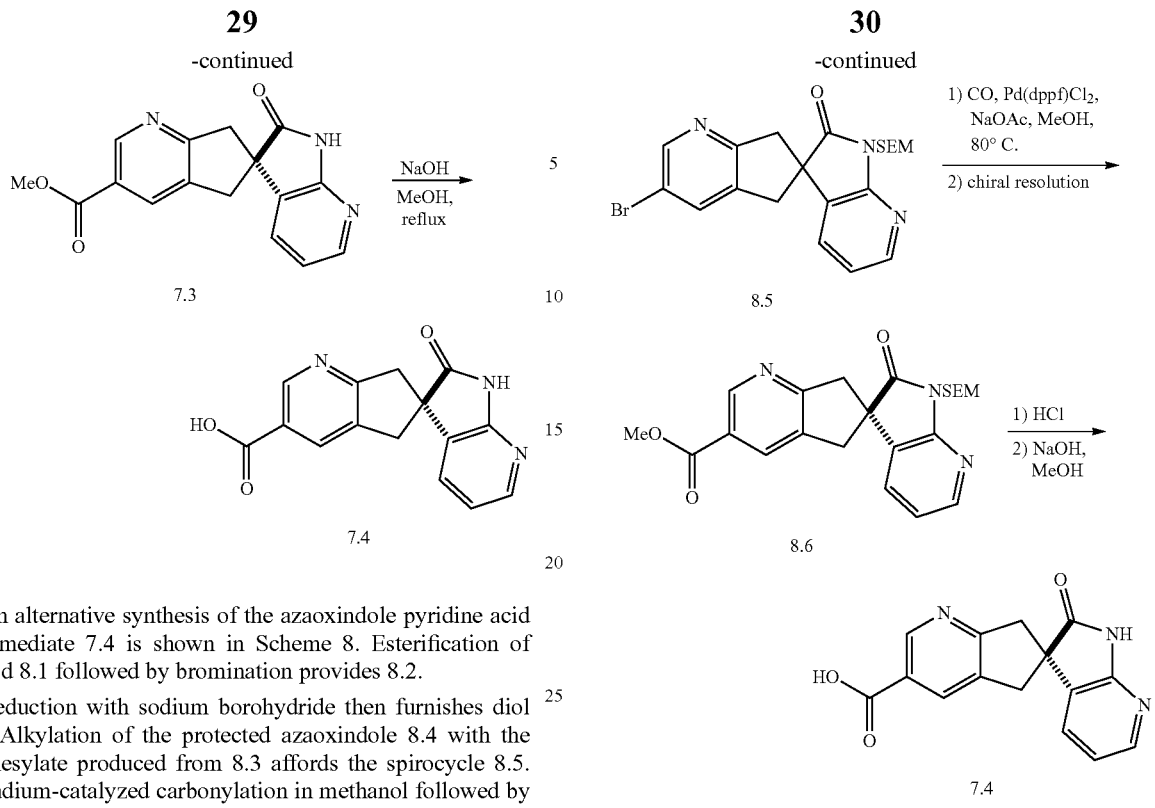

An alternative synthesis of the azaoxindole pyridine acid intermediate 7.4 is shown in Scheme 8. Esterification of diacid 8.1 followed by bromination provides 8.2.

Reduction with sodium borohydride then furnishes diol 8.3. Alkylation of the protected azaoxindole 8.4 with the bismesylate produced from 8.3 affords the spirocycle 8.5. Palladium-catalyzed carbonylation in methanol followed by chiral resolution gives ester 8.6 as a single enantiomer. Removal of the SEM protecting group under acidic conditions and hydrolysis of the ester using sodium hydroxide then provides 7.4.

A synthetic route to diazaoxindole carboxylic acid intermediate 9.7 is shown in Scheme 9. Esterification of acid 9.1 is followed by vinylation under palladium catalysis to afford divinyl pyridine 9.2. Ozonolysis with a borohydride reductive workup then yields diol 9.3. After mesylation and treatment with sodium chloride, the resulting dichloro intermediate 9.4 can be alkylated with oxindole 9.5 under basic conditions to give spirocycle 9.6, following chiral resolution of the enantiomers. Dechlorination under buffered hydrogenation conditions and acidic deprotection affords acid 9.7.

SCHEME 8

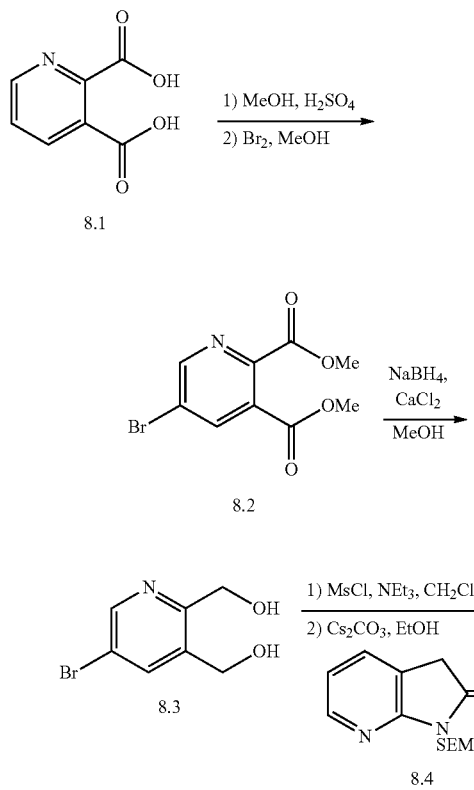

SCHEME 9

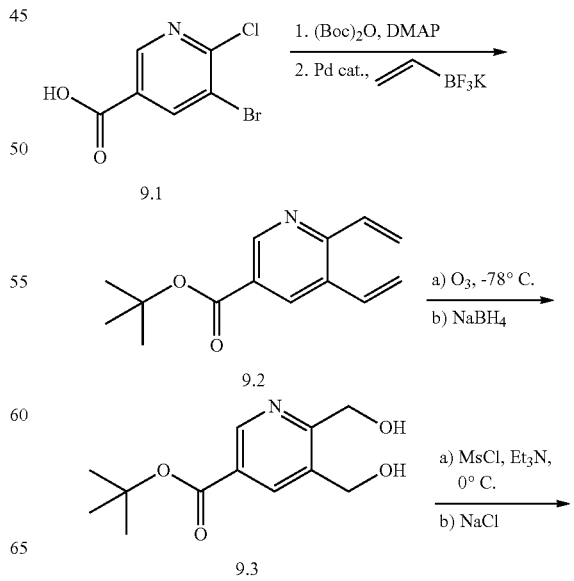

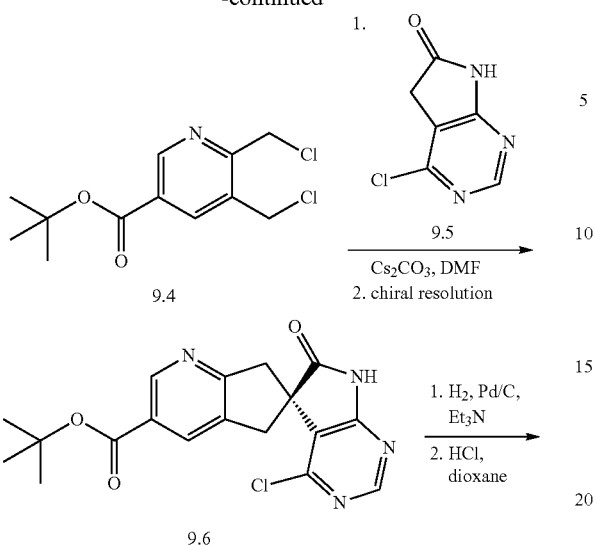

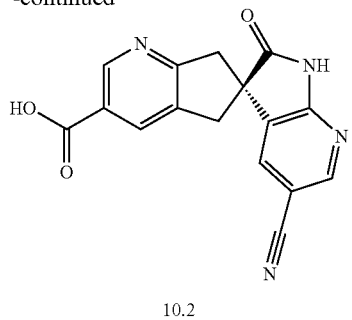

Scheme 11 illustrates conditions that can be used for the coupling of 3-aminopiperidinone intermediates, such as 11.1, and carboxylic acid intermediate 11.2, to produce, in this instance, amides 11.3. These standard coupling conditions are representative of the methods used to prepare the compounds of the present invention.

SCHEME 11

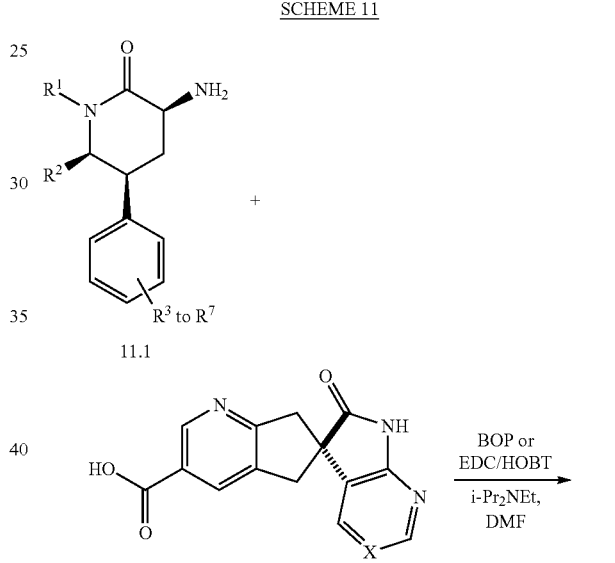

Useful derivatives of the intermediates described herein may be prepared using well-precedented methodology. One such example is illustrated in Scheme 10, in which the aza-oxindole intermediate 7.4 is converted to the corresponding nitrile derivative 10.2, which may be used to prepare compounds of the present invention. Bromination of 7.4 with N-bromosuccinimide in boron trifluoride dihydrate provides the bromo derivative 10.1, which may be converted to the desired nitrile 10.2 using zinc cyanide and a palladium catalyst as shown.

SCHEME 10

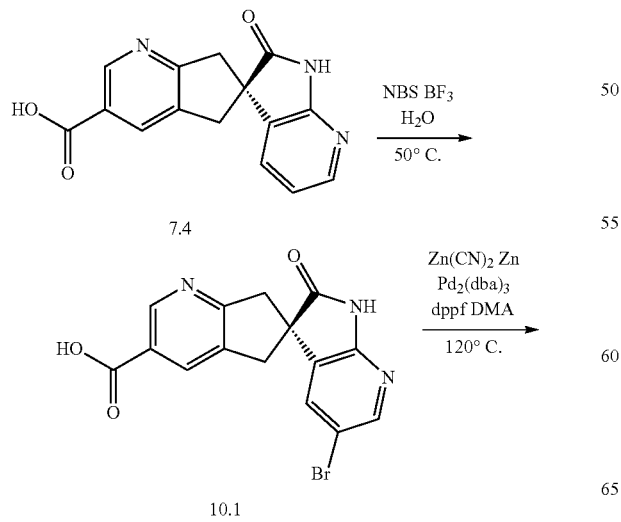

In some cases, various protecting group strategies familiar to one skilled in the art of organic synthesis may be employed to allow preparation of a particular compound of the present invention.

It is understood that alternative methodologies may also be employed in the synthesis of these key intermediates. For instance, racemic reaction sequences may be utilized, followed by chiral separations at appropriate steps to provide compounds of the present invention. The exact choice of reagents, solvents, temperatures, and other reaction conditions, depends upon the nature of the intended product. In some cases, appropriate protecting group strategies may be used.

In some cases the final product may be further modified, for example, by manipulation of substituents. These manipulations may include, but are not limited to, reduction, oxidation, alkylation, acylation, and hydrolysis reactions which are commonly known to those skilled in the art.

In some cases the order of carrying out the foregoing reaction schemes may be varied to facilitate the reaction or to avoid unwanted reaction products. Additionally, various protecting group strategies may be employed to facilitate the reaction or to avoid unwanted reaction products. The following examples are provided so that the invention might be more fully understood. These examples are illustrative only and should not be construed as limiting the invention in any way.

INTERMEDIATE 1

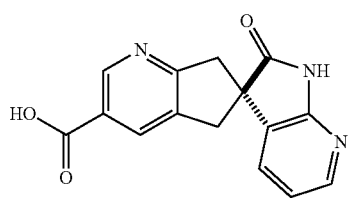

(6S)-2'-Oxo-1',2',5,7-tetrahydrospiro[cyclopenta[b]pyridine-6,3'-pyrrolo[2,3-b]pyridine]-3-carboxylic acid The title compound can be prepared by either Method I or Method II as described below.
Method I:

Step A: (6S)-3-Iodo-5,7-dihydrospiro[cyclopenta[b]pyridine-6,3'-pyrrolo[2,3-b]pyridin]-2'(1'H)-one A solution of sodium nitrite (36.1 g, 523 mmol) in water (20 mL) was added dropwise over 5 min to a solution of (6S)-3-amino-5,7-dihydrospiro[cyclopenta[b]pyridine-6,3'-pyrrolo[2,3-b]pyridin]-2'(1'H)-one (prepared according to the procedures described in WO2008/020902, 66.0 g, 262 mmol) and p-toluenesulfonic acid (149 g, 785 mmol) in acetonitrile (650 mL) at 23° C. After stirring for 30 min, a solution of potassium iodide (109 g, 654 mmol) in water (20 mL) was added over 5 min. The resulting mixture was stirred at 23° C. for 40 min, then diluted with water (1 L) and basified by the addition of solid NaOH (33.0 g, 824 mmol) with stirring. Iodine by-product was reduced by the addition of 10% aqueous sodium thiosulfate solution and stirring for an additional 30 min. The solids were collected by filtration, washed with water, and dried under nitrogen atmosphere to give the title compound, which was used without further purification. MS: m/z=363.9 (M+1).

Step B: Methyl (6S)-2'-oxo-1',2',5,7-tetrahydrospiro[cyclopenta[b]pyridine-6,3'-pyrrolo[2,3-b]pyridine]-3-carboxylate A solution of (6S)-3-iodo-5,7-dihydrospiro[cyclopenta[b]pyridine-6,3'-pyrrolo[2,3-b]pyridin]-2'(1'H)-one (51.0 g, 140 mmol), sodium acetate (23.0 g, 281 mmol) and dichloro 1,1'-bis(diphenylphosphino)ferrocene palladium(II) dichloromethane adduct (2.9 g, 3.5 mmol) in MeOH (560 mL) was pressurized to 120 psi of CO at 23° C. and then heated at 80° C. for 12 h with stirring. The reaction mixture was diluted with water (1 L), and the precipitate collected by filtration, washed with water, and dried under nitrogen atmosphere to give the title compound, which was used without further purification. MS: m/z=296.1 (M+1).

Step C: (6S)-2'-Oxo-1',2',5,7-tetrahydrospiro[cyclopenta[b]pyridine-6,3'-pyrrolo[2,3-b]pyridine]-3-carboxylic acid A mixture of methyl (6S)-2'-oxo-1',2',5,7-tetrahydrospiro[cyclopenta[b]pyridine-6,3'-pyrrolo[2,3-b]pyridine]-3-carboxylate (30.0 g, 102 mmol) and aqueous 6 N sodium hydroxide solution (50.8 mL, 305 mmol) in MeOH (920 mL) was heated at reflux for 1 h. The mixture was allowed to cool to 23° C. before it was acidified to pH~6 with aqueous 1 N hydrochloric acid solution, resulting in a black precipitate which was removed by filtration. The filtrate was concentrated under reduced pressure to a volume of ~100 mL and then partitioned between water (500 mL) and 2-methyltetrahydrofuran (2-MeTHF, 250 mL). The aqueous layer was extracted with 2-MeTHF (5×250 mL), and the combined organic layers were dried over sodium sulfate and concentrated to provide the title compound. MS: m/z=282.0 (M+1).
Method II:

Step A: Dimethyl 5-bromopyridine-2,3-dicarboxylate

Concentrated sulfuric acid (1 L, 18.7 mol) was added slowly over 10 min to a suspension of pyridine-2,3-dicarboxylic acid (5.00 kg, 29.9 mol) in methanol (50 L), dissolving the suspension. The resulting mixture was heated at reflux for 48 h then cooled to 40° C. Bromine (8.0 kg, 50 mol) was added slowly over 2 h in 1-kg portions, keeping the temperature below 55° C. The reaction mixture was then heated at 55° C. for 24 h, cooled to 50° C. and additional Br$_2$ (4.0 kg, 25 mol) was added slowly over 1 h in 1-kg portions, keeping temperature below 55° C. The reaction mixture was heated at 55° C. for 24 h, concentrated to a minimum volume (internal temp ~30° C., solution may occasionally foam), then diluted with isopropyl acetate (50 L) and washed with a saturated aqueous sodium sulfite solution (3×20 L) (final extract is ~pH 8) followed by water (20 L). The organic layer was concentrated to approximately 15 L then diluted with heptane (40 L). The resulting slurry was stirred for 24 h at 23° C. The solids were filtered, washed with heptane (10 L), and dried to give the title compound.

Step B: (5-Bromopyridine-2,3-diyl)dimethanol

Sodium borohydride (15.9 g, 420 mmol) was added portionwise over 30 min to a solution of dimethyl 5-bromopyridine-2,3-dicarboxylate (20 g, 73 mmol) in ethanol (460 mL) precooled to 0° C. A solution of calcium chloride (23.3 g, 209 mmol) in 150 mL was added slowly at 0° C., and the reaction mixture was warmed to 23° C. and stirred overnight. Excess sodium borohydride was quenched by slow addition of aqueous 2 N HCl solution (230 mL, 460 mmol), followed by a stirring at 23° C. for 2 h. The mixture was concentrated to dryness. Saturated aqueous sodium bicarbonate solution was added to the residue until a pH of approximately 7 was reached. The aqueous mixture was extracted with 2-methyltetrahydrofuran (4×200 mL). The combined organic layers were dried over sodium sulfate then treated with a solution of 4 N HCl in dioxane (25 mL, 100 mmol). The resulting solid was filtered, washed with 2-methyltetrahydrofuran, and dried to give the title compound as a hydrochloride salt. MS: m/z=218.1 (M+1).

Step C: (5-Bromopyridine-2,3-diyl)dimethanediyl dimethanesulfonate

A slurry of (5-bromopyridine-2,3-diyl)dimethanol hydrochloride (12.9 g, 59.2 mmol) in tetrahydrofuran (400 mL) at 0° C. was treated with triethylamine (37.1 mL, 266 mmol). To the resulting mixture was added portionwise methanesulfonic anhydride (30.9 g, 177 mmol), keeping temperature below 5° C. The reaction mixture was stirred at 0° C. for 1 h, then partitioned between saturated aqueous sodium bicarbonate solution (500 mL) and ethyl acetate (500 mL). The organic layer was washed saturated aqueous sodium bicarbonate solution, dried over magnesium sulfate, and concentrated to give the title compound. MS: m/z=376.0 (M+1).

Step D: 3-Bromo-1'-{[2-(trimethylsilyl)ethoxy]methyl}-5,7-dihydrospiro[cyclopenta[b]pyridine-6,3'-pyrrolo[2,3-b]pyridin]-2'(1'H)-one (5-Bromopyridine-2,3-diyl)dimethanediyl dimethanesulfonate (17.0 g, 45.4 mmol) was added to a mixture of 1-{[2-(trimethylsilyl)ethoxy]methyl}-1,3-dihydro-2H-pyrrolo[2,3-b]pyridin-2-one (prepared according to the procedures described in WO2008/020902, 14.0 g, 53.0 mmol) and cesium carbonate (49.0 g, 150 mmol) in ethanol (500 mL) 23° C., and the resulting mixture was stirred for 20 h. The reaction mixture was concentrated then partitioned between ethyl acetate (500 mL) and water (500 mL). The organic layer was dried over magnesium sulfate and concentrated. The residue was purified via silica gel chromatography (heptane initially, grading to 100% EtOAc) to give the title compound. MS: m/z=448.1 (M+1).

Step E: Methyl (6S)-2'-oxo-1'-{[2-(trimethylsilyl)ethoxy]methyl}-1',2',5,7-tetrahydrospiro[cyclopenta[b]pyridine-6,3'-pyrrolo[2,3-b]pyridine]-3-carboxylate A mixture of 3-bromo-1'-{[2-(trimethylsilyl)ethoxy]methyl}-5,7-dihydrospiro[cyclopenta[b]pyridine-6,3'-pyrrolo[2,3-b]pyridin]-2'(1'H)-one (22.0 g, 49.3 mmol), PdCl$_2$(dppf).CH$_2$Cl$_2$ (2.012 g, 2.46 mmol), and sodium acetate (8.1 g, 99 mmol) in in methanol (150 mL) was pressurized to 300 psi of carbon monoxide and then heated at 85° C. for 72 h. The reaction mixture was allowed to cool then concentrated. The residue was purified via silica gel chromatography (heptane initially, grading to 100% EtOAc) to give the title compound as a racemic mixture. MS: m/z=426.1 (M+1). Resolution of the enantiomers by supercritical fluid chromatography (SFC) using a ChiralPak® AD-H column and eluting with 40% ethanol in CO$_2$ (0.05% diethylamine as modifier) provided the title compound as the second enantiomer to elute.

Step F: (6S)-2'-Oxo-1',2',5,7-tetrahydrospiro[cyclopenta[b]pyridine-6,3'-pyrrolo[2,3-b]pyridine]-3-carboxylic acid A solution of methyl (6S)-2'-oxo-1'-{[2-(trimethylsilyl)ethoxy]methyl}-1',2',5,7-tetrahydrospiro[cyclopenta[b]pyridine-6,3'-pyrrolo[2,3-b]pyridine]-3-carboxylate (238 g, 559 mmol) in methanol (2 L) was saturated with HCl gas, allowing temperature to increase to 55° C. The reaction mixture was cooled to 23° C., stirred for 20 h, then concentrated. Aqueous 10 N sodium hydroxide (400 mL, 4 mol) was added to a solution of the residue in methanol (2 L), and the resulting mixture was heated at reflux for 2 h. The solution was cooled to 23° C. and the pH was adjusted to 3 with concentrated HCl. The resulting solid was filtered, washed with water then heptane, and dried to give the title compound. MS: m/z=282.2 (M+1).

INTERMEDIATE 2

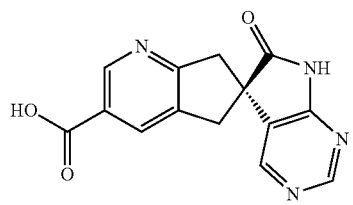 [SMILES: O=C(O)c1cnc2c(c1)C[C@@]1(C2)C(=O)Nc2ncncc21]

(6S)-6'-Oxo-5,6',7,7'-tetrahydrospiro[cyclopenta[b]pyridine-6,5'-pyrrolo[2,3-d]pyrimidine]-3-carboxylic acid Step A: tert-Butyl 5-bromo-6-chloropyridine-3-carboxylate To a solution of 5-bromo-6-chloronicotinic acid (25.0 g, 106 mmol) in tetrahydrofuran (1.06 L) was added di-tert-butyl dicarbonate (69.2 g, 317 mmol) followed by 4-dimethylaminopyridine (12.9 g, 106 mmol). After 16 h, the mixture was diluted with water and aqueous hydrochloric acid was added (106 mL, 1 M, 106 mmol). The mixture was extracted with ethyl acetate (3×). The combined organic extracts were washed with brine (3×), dried over magnesium sulfate, filtered and concentrated. Purification by silica gel chromatography (100% dichloromethane→10% methanol/dichloromethane) gave the title compound. MS: m/z=294.1 (M+1).

Step B: tert-Butyl 5,6-diethenylpyridine-3-carboxylate

To a solution of tert-butyl 5-bromo-6-chloropyridine-3-carboxylate (24.0 g, 82.0 mmol) in acetonitrile (615 mL) and water (205 mL) were added potassium vinyltrifluoroborate (33.0 g, 246 mmol) and triphenylphosphine-3,3',3''-trisulfonic acid trisodium salt (4.20 g, 7.38 mmol). Diisopropylamine (88.0 mL, 615 mmol) was added followed by palladium(II) acetate (0.553 g, 2.46 mmol). The mixture was heated to 75° C. After 16 h, the mixture was cooled to ambient temperature and saturated sodium bicarbonate was added. The mixture was washed with dichloromethane (3×) and the combined organics were washed with water, brine, and dried with magnesium sulfate, filtered and concentrated. Purification by silica gel chromatography (100% dichloromethane→5% methanol/dichloromethane) gave the title compound. MS: m/z=232.3 (M+1).

Step C: tert-Butyl 5,6-bis(hydroxymethyl)pyridine-3-carboxylate

To a solution of tert-butyl 5,6-diethenylpyridine-3-carboxylate (19.0 g, 82 mmol) in dichloromethane (821 mL) at −78° C. was added ozone gas. The ozone bubbled though the solution until saturated (1 h). Nitrogen gas was then bubbled through the solution. The mixture was diluted with methanol (821 mL) and sodium borohydride (7.77 g, 205 mmol) was added. After 15 min, the mixture was quenched with saturated aqeuous sodium bicarbonate and washed with dichloromethane (3×). The combined organics were washed with brine, dried with magnesium sulfate, filtered and concentrated. Purification by silica gel chromatography (100% dichloromethane→15% methanol/dichloromethane) gave the title compound. MS: m/z=240.3 (M+1).

Step D: tert-Butyl 5,6-bis(chloromethyl)pyridine-3-carboxylate

To a solution of tert-butyl 5,6-bis(hydroxymethyl)pyridine-3-carboxylate (5.87 g, 24.5 mmol) in N,N-dimethylformamide (146 mL) at 0° C. was added triethylamine (13.7 mL, 98 mmol) followed by methanesulfonic anhydride (12.8 g, 73.6 mmol). After 15 min, water (29.2 mL) and sodium chloride (8.60 g, 147 mmol) were added and the mixture warmed to ambient temperature. After 16 h, saturated aqueous sodium bicarbonate was added and the mixture was extracted with ethyl acetate (3×). The combined organics were washed with water (3×) and then brine (3×), dried with magnesium sulfate, filtered and concentrated. Purification by silica gel chromatography (100% dichloromethane→10% methanol/dichloromethane) gave the title compound. MS: m/z=276.2 (M+1).

Step E: tert-Butyl (6S)-4'-chloro-6'-oxo-5,6',7,7'-tetrahydrospiro[cyclopenta[b]pyridine-6,5'-pyrrolo[2,3-d]pyrimidine]-3-carboxylate To a solution of tert-butyl 5,6-bis(chloromethyl)pyridine-3-carboxylate (1.80 g, 6.52 mmol) in N,N-dimethylformamide (93.0 mL) was added 4-chloro-5,7-dihydro-6H-pyrrolo[2,3-d]pyrimidin-6-one (1.80 g, 10.62 mmol), cesium carbonate (3.65 g, 11.21 mmol), and sodium bromide (0.671 g, 6.52 mmol). After 30 min, saturated aqueous sodium bicarbonate was added and the mixture was washed with ethyl acetate (3×). The combined organics were washed with water (3×), brine (3×) and were dried with magnesium sulfate, filtered and concentrated. Purification by silica gel chromatography (100% dichloromethane→10% methanol/dichloromethane) then a second purification by silica gel chromatography (100% dichloromethane→30% ethyl acetate/dichloromethane) gave the title compound as a racemic mixture. Chiral separation of the individual enantiomers was accomplished by use of HPLC using a 10 cm ChiralPak® AD column (60% EtOH/hexanes with 0.1% diethylamine) to give the title compound as the 1$^{st}$ eluting enantiomer. MS: m/z=373.2 (M+1).

Step F: tert-Butyl (6S)-6'-oxo-5,6',7,7'-tetrahydrospiro[cyclopenta[b]pyridine-6,5'-pyrrolo[2,3-d]pyrimidine]-3-carboxylate To a solution of tert-butyl (6S)-4'-chloro-6'-oxo-5,6',7,7'-tetrahydrospiro[cyclopenta[b]pyridine-6,5'-pyrrolo[2,3-d]pyrimidine]-3-carboxylate (200 mg, 0.537 mmol) in dry ethyl acetate (5.37 mL) was added triethylamine (299 μL, 2.15 mmol) and palladium on carbon (571 mg, 10%, 0.537 mmol). The reaction was placed on a Parr apparatus at 50 psi hydrogen gas. After 16 h, the reaction mixture was filtered under a nitrogen atmosphere through Celite®, washing with ethyl acetate. The filtrate was concentrated to give the title compound, along with one equivalent of triethylamine hydrochloride. MS: m/z=339.3 (M+1).

Step G: (6S)-6'-Oxo-5,6',7,7'-tetrahydrospiro[cyclopenta[b]pyridine-6,5'-pyrrolo[2,3-d]pyrimidine]-3-carboxylic acid To solid tert-butyl (6S)-6'-oxo-5,6',7,7'-tetrahydrospiro[cyclopenta[b]pyridine-6,5'-pyrrolo[2,3-d]pyrimidine]-3-carboxylate (255 mg, 0.536 mmol) containing one equivalent of triethylamine hydrochloride (from previous step) was added hydrochloric acid solution (20 mL, 4 M in dioxane). After 16 h, the mixture was concentrated to give the title compound as a bis hydrochloric acid salt with one equivalent of triethylamine hydrochloride. MS: m/z=283.2 (M+1). $^1$H NMR (500 MHz, DMSO): δ 11.75 (s, 1H); 9.50 (s, 1H); 8.90 (s, 1H); 8.80 (s, 1H); 8.40 (s, 1H); 8.20 (s, 1H); 3.50-3.40 (m, 4H).

INTERMEDIATE 3

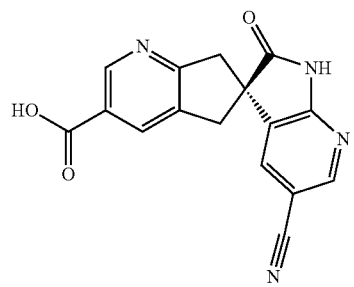 [SMILES: N#Cc1cnc2c(c1)[C@@]1(Cc3cc(C(=O)O)cnc3C1)C(=O)N2]

(6S)-5'-Cyano-2'-oxo-1',2',5,7-tetrahydrospiro[cyclopenta[b]pyridine-6,3'-pyrrolo[2,3-b]pyridine]-3-carboxylic acid Step A: (6S)-5'-Bromo-2'-oxo-1',2',5,7-tetrahydrospiro[cyclopenta[b]pyridine-6,3'-pyrrolo[2,3-b]pyridine]-3-carboxylic acid To a stirred mixture of (6S)-2'-oxo-1',2',5,7-tetrahydrospiro[cyclopenta[b]pyridine-6,3'-pyrrolo[2,3-b]pyridine]-3-carboxylic acid (described in Intermediate 1) (1.03 g, 3.66 mmol) in boron trifluoride dihydrate (12 mL) was added N-bromosuccinimide (1.37 g, 7.70 mmol) and the resulting mixture was heated at 50° C. for 2 h. The reaction mixture was cooled to ambient temperature and N-bromosuccinimide (1.83 g, 10.3 mmol) was added. The resulting mixture was heated at 50° C. for 16 h, allowed to cool to ambient temperature, and the crude mixture was purified by reversed-phase HPLC on a C-18 column, eluting with a gradient of H$_2$O:CH$_3$CN:TFA—95:5:0.1 to 65:35:0.1, to give the title compound. MS: m/z=361.9 (M+1).

Step B: (6S)-5'-Cyano-2'-oxo-1',2',5,7-tetrahydrospiro[cyclopenta[b]pyridine-6,3'-pyrrolo[2,3-b]pyridine]-3-carboxylic acid Argon was bubbled through a stirred mixture of (6S)-5'-bromo-2'-oxo-1',2',5,7-tetrahydrospiro[cyclopenta[b]pyridine-6,3'-pyrrolo[2,3-b]pyridine]-3-carboxylic acid (352 mg, 0.98 mmol), zinc cyanide (150 mg, 1.28 mmol), and zinc (20 mg, 0.31 mmol) in N,N-dimethylacetamide (6 mL) for 10 min. To the resulting mixture was added tris(dibenzylideneacetone)dipalladium(0) (20 mg, 0.022 mmol) and 1,1'-bis(diphenylphosphino)ferrocene (16 mg, 0.029 mmol) and argon was bubbled through the mixture for an additional 5 min. The reaction mixture was heated at 120° C. for 18 h, cooled to ambient temperature, and purified directly by reversed-phase HPLC on a C-18 column, eluting with a gradient of $H_2O:CH_3CN:TFA$—95:5:0.1 to 65:35:0.1, to give the title compound. MS: m/z=306.9 (M+1); $^1$H NMR (400 MHz, DMSO-$d_6$) δ 11.71 (s, 1H), 8.91 (d, 1H, J=1.9 Hz), 8.61 (d, 1H, J=2.0 Hz), 8.14 (d, 1H, J=1.8 Hz), 8.03 (d, 1H, J=1.8 Hz), 3.49-3.34 (m, 4H).

INTERMEDIATE 4

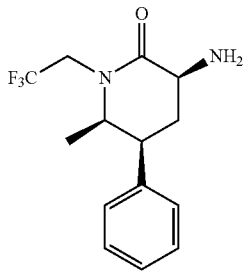 [SMILES: C[C@@H]1[C@H](c2ccccc2)C[C@H](N)C(=O)N1CC(F)(F)F]

(3S,5S,6R)-3-Amino-6-methyl-5-phenyl-1-(2,2,2-trifluoroethyl)piperidin-2-one

Step A: Methyl 2-[(tert-butoxycarbonyl)amino]-4-(3-chlorophenyl)-5-oxohexanoate

A mixture of cesium carbonate (9.80 g, 30.1 mmol) and methyl N-(tert-butoxycarbonyl)-3-iodo-D-alaninate (9.90 g, 30.1 mmol) in DMF (75 mL) was stirred at 23° C. for 45 min before 1-(3-chlorophenyl)propan-2-one (6.09 g, 36.1 mmol) and additional cesium carbonate (9.80 g, 30.1 mmol) were added. The resulting mixture was stirred for 2.5 h. The majority of the DMF was then removed under reduced pressure at a bath temperature of <40° C. The concentrated mixture was partitioned between water (500 mL) and ethyl acetate (2×200 mL). The combined organic layers were washed with brine, dried over sodium sulfate and concentrated to give the title compound as a 1:1 racemic mixture of diastereomers, which was used without further purification. MS: m/z=314.1 (M−t-Bu+1).

Step B: tert-Butyl [(3S,5S,6R)-5-(3-chlorophenyl)-6-methyl-2-oxo-1-(2,2,2-trifluoroethyl)piperidin-3-yl]carbamate A slurry of methyl 2-[(tert-butoxycarbonyl)amino]-4-(3-chlorophenyl)-5-oxohexanoate as a 1:1 racemic mixture of diastereomers (11.1 g, 30.0 mmol), 2,2,2-trifluoroethylamine (9.59 mL, 120 mmol), acetic acid (10.3 mL, 180 mmol), sodium triacetoxyborohydride (25.4 g, 120 mmol), and flame-dried 4 Å molecular sieves (50 g) in 1,2-dichloroethane (300 mL) was stirred at 23° C. for 8 h. Additional 2,2,2-trifluoroethylamine (9.59 mL, 120 mmol), acetic acid (10.3 mL, 180 mmol), and sodium triacetoxyborohydride (25.4 g, 120 mmol) were added and stirring was continued for 20 h. The reaction mixture was diluted with dichloromethane (200 mL) then poured into water (500 mL). Molecular sieves were removed by filtration, and the organic layer was washed with water (3×500 mL), dried over sodium sulfate, and concentrated. A solution of the residue in ethanol (200 mL) was stirred in the presence of solid potassium carbonate (12.4 g, 90 mmol) at 60° C. for 2 h, then 23° C. for 16 h. The bulk of the ethanol was removed under reduced pressure and the remaining slurry was then partitioned between water (500 mL) and ethyl acetate (300 mL). The organic layer was washed with brine, dried over sodium sulfate and concentrated. The residue was crystallized from a 2:1 mixture of hexane and ethyl ether to give the title compound as a racemate. The enantiomers were separated using normal-phase HPLC using a ChiralPak® AD column, eluting with 40% hexane in ethanol initially, stepping to 20% hexane in ethanol (0.1% diethylamine used as a modifier) to afford the title compound as the second enantiomer to elute. MS: m/z=421.2 (M+1).

Step C: (3S,5S,6R)-3-Amino-6-methyl-5-phenyl-1-(2,2,2-trifluoroethyl)piperidin-2-one A mixture of tert-butyl [(3S,5S,6R)-5-(3-chlorophenyl)-6-methyl-2-oxo-1-(2,2,2-trifluoroethyl)piperidin-3-yl]carbamate (2.75 g, 6.53 mmol) and 20 wt. % palladium hydroxide on carbon (~50 wt. % wet, 700 mg, 0.50 mmol) in methanol (100 mL) was stirred under a hydrogen balloon at 23° C. for 16 h. The catalyst was removed by filtration through Celite® and washed thoroughly with methanol and ethyl acetate. Following concentration of the filtrate, a solution of the residue in ethyl acetate (100 mL) pre-cooled to 0° C. was sparged with HCl gas for ~1 min. The ice-bath was removed and the acidic solution was allowed to warm to 23° C. as stirring was continued for 2 h. The mixture was then concentrated to dryness to afford the title compound as a hydrochloride salt. HRMS: m/z=287.1361, calculated m/z=287.1366 for $C_{14}H_{18}F_3N_2O$. $^1$H NMR (500 MHz, $CD_3OD$) δ 7.39 (t, 2H, J=7.3 Hz), 7.31 (t, 1H, J=7.3 Hz), 7.27 (d, 2H, J=7.3 Hz), 4.81-4.73 (m, 1H), 4.24 (dd, 1H, J=12.0, 6.8 Hz), 3.94 (p, 1H, J=6.0 Hz), 3.76-3.67 (m, 2H), 2.56 (q, 1H, J=12.7 Hz), 2.42 (m, 1H), 1.00 (d, 3H, J=6.3 Hz).

INTERMEDIATE 5

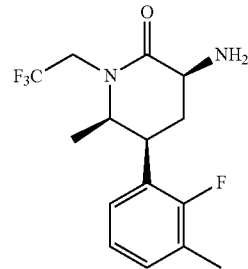 [SMILES: Cc1cccc([C@@H]2C[C@H](N)C(=O)N(CC(F)(F)F)[C@@H]2C)c1F]

(3S,5S,6R)-3-Amino-5-(2-fluoro-3-methylphenyl)-6-methyl-1-(2,2,2-trifluoroethyl)piperidin-2-one Step A: 5-Bromo-6-methyl-3-nitro-1-(2,2,2-trifluoroethyl)pyridin-2(1H)-one A mixture of 5-bromo-6-methylpyridin-2(1H)-one (10.0 g, 53.2 mmol), cesium carbonate (20.8 g, 63.8 mmol), and 2,2,2-trifluoroethyl methanesulfonate (18.5 g, 80.0 mmol) in dioxane (266 mL) was heated at 66° C. for 1.5 h. The mixture was allowed to cool to 23° C., then diluted with dichloromethane (266 mL). Nitronium tetrafluoroborate (21.2 g, 160 mmol) was added and the resulting mixture was stirred for 16 h. The mixture was then partitioned between half-saturated aqueous sodium chloride solution (500 mL) and ethyl acetate (1 L). The organic layer was washed with brine, dried over sodium sulfate and concentrated. The residue was purified by flash column chromatography on silica gel, eluting with hexane initially, grading to 50% EtOAc in hexane to provide the title compound. MS: m/z=315.0 (M+1).

Step B: 5-(2-Fluoro-3-methylphenyl)-6-methyl-3-nitro-1-(2,2,2-trifluoroethyl)pyridin-2(1H)-one A deoxygenated mixture of 5-bromo-6-methyl-3-nitro-1-(2,2,2-trifluoroethyl)pyridin-2(1H)-one (2.00 g, 6.35 mmol), (2-fluoro-3-methylphenyl)boronic acid (1.95 g, 12.7 mmol), potassium fluoride (2.43 g, 41.9 mmol), and bis(tri-tert-butylphosphine) palladium(0) (0.333 g, 0.652 mmol) in THF (32 mL) was heated at 66° C. for 30 min. The reaction mixture was allowed to cool to 23° C., then partitioned between water (200 mL) and ethyl acetate (200 mL). The organic layer was washed with brine, dried over sodium sulfate and concentrated. The residue was purified by flash column chromatography on silica gel, eluting with hexane initially, grading to 50% EtOAc in hexanes to give the title compound. MS: m/z=345.1 (M+1).

Step C: (3S,5S,6R)-3-Amino-5-(2-fluoro-3-methylphenyl)-6-methyl-1-(2,2,2-trifluoroethyl)piperidin-2-one A mixture of 5-(2-fluoro-3-methylphenyl)-6-methyl-3-nitro-1-(2,2,2-trifluoroethyl)pyridin-2(1H)-one (1.95 g, 5.66 mmol), platinum(IV) oxide (0.643 g, 2.83 mmol), and concentrated aqueous hydrochloric acid solution (12 M, 4.72 mL, 56.6 mmol) in methanol (57 mL) was shaken under 50 psi of hydrogen at 23° C. for 5 h. The catalyst was removed by filtration through Celite® and washed thoroughly with methanol. The filtrate was concentrated, and the residue was partitioned between ethyl acetate and saturated aqueous sodium bicarbonate solution. The organic layer was washed with brine, dried over sodium sulfate and concentrated. The residue was purified by flash column chromatography on silica gel, eluting with dichloromethane initially, grading to 5% MeOH (basified 0.1% concentrated aqueous ammonium hydroxide solution) in dichloromethane to give the title compound as a racemate. The enantiomers were separated by normal-phase HPLC using a ChiralCel® OD column, eluting with 40% hexane in ethanol (0.1% diethylamine used as a modifier) to afford the title compound as the second enantiomer to elute. MS: m/z=319.2 (M+1).

INTERMEDIATE 6

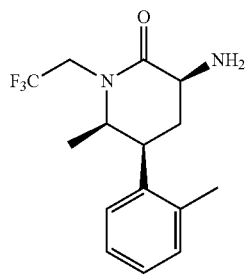 [SMILES: Cc1ccccc1[C@@H]1C[C@H](N)C(=O)N(CC(F)(F)F)[C@@H]1C]

(3S,5S,6R)-3-Amino-6-methyl-5-(2-methylphenyl)-1-(2,2,2-trifluoroethyl)piperidin-2-one Step A: Methyl N-(tert-butoxycarbonyl)-4-(2-methylphenyl)-5-oxonorleucinate To a solution of methyl N-(tert-butoxycarbonyl)-3-iodo-D-alaninate (1.58 g, 4.80 mmol) in DMF (24 mL) was added cesium carbonate (1.56 g, 4.80 mmol) and the mixture was stirred at 23° C. for 45 min. 1-(2-Methylphenyl)-propan-2-one (0.783 g, 5.28 mmol) and cesium carbonate (2.35 g, 7.20 mmol) were added and the resulting mixture was stirred for 18 h. The mixture was filtered and water was added to the filtrate. The mixture was extracted with ethyl acetate (3×). The combined organic extracts were washed with water (3×), brine, dried over sodium sulfate, filtered and concentrated. Purification by silica gel chromatography (5% ethyl acetate→40% ethyl acetate/hexane) gave the title compound. MS: m/z=350.1 (M+1).

Step B: tert-Butyl [(3S,5S,6R)-6-methyl-5-(2-methylphenyl)-2-oxo-1-(2,2,2-trifluoroethyl)piperidin-3-yl]carbamate To a solution of methyl N-(tert-butoxycarbonyl)-4-(2-methylphenyl)-5-oxonorleucinate (1.60 g, 4.58 mmol) in dichloroethane (23 mL) were added glacial acetic acid (0.524 mL, 9.16 mmol), 2,2,2-trifluoroethylamine (1.83 mL, 22.9 mmol) and 4 Å molecular sieves (500 mg). The mixture was stirred at 23° C. for 20 min and then sodium triacetoxyborohydride (4.85 g, 22.89 mmol) was added. The mixture was stirred at 23° C. for 18 h. The mixture was diluted with water and extracted with ethyl acetate (3×). Molecular sieves were removed by filtration and the combined organic extracts were washed with water, brine, dried over sodium sulfate, filtered and concentrated. A solution of the residue in ethanol (45 mL) was stirred in the presence of solid potassium carbonate (1.86 g, 13.49 mmol) at 60° C. for 2 h. The bulk of the ethanol was removed under reduced pressure and the remaining slurry was then partitioned between water (25 mL) and ethyl acetate (150 mL). The organic layer was washed with brine, dried over sodium sulfate and concentrated. Purification by silica gel chromatography (5% ethyl acetate→50% ethyl acetate/hexane) was followed by separation of the enantiomers using normal-phase HPLC using a ChiralPak® AD column, eluting with 20% hexane in ethanol (0.1% diethylamine used as a modifier) to afford the title compound as the second enantiomer to elute. MS: m/z=423.2 (M+Na).

Step C: (3S,5S,6R)-3-Amino-6-methyl-5-(2-methylphenyl)-1-(2,2,2-trifluoroethyl)piperidin-2-one A solution of tert-butyl [(3S,5S,6R)-6-methyl-5-(2-methylphenyl)-2-oxo-1-(2,2,2-trifluoroethyl)piperidin-3-yl]carbamate (152 mg, 0.37 mmol) in ethyl acetate (10 mL), precooled to 0° C. was sparged with HCl gas for ~1 min. The reaction mixture was allowed to sit for 30 min at 0° C. The

INTERMEDIATE 7

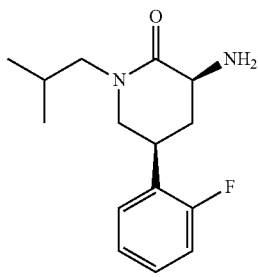 [SMILES: CC(C)CN1C[C@H](c2ccccc2F)C[C@H](N)C1=O]

(3S,5S)-3-Amino-5-(2-fluorophenyl)-1-(2-methyl-propyl)piperidin-2-one

Step A: Methyl N-(tert-butoxycarbonyl)-4-(2-fluorophenyl)-5-nitrilonorvalinate To a solution of methyl N-(tert-butoxycarbonyl)-3-iodo-D-alaninate (5.00 g, 15.19 mmol) in DMF (20 mL) was added cesium carbonate (5.44 g, 16.71 mmol) and the mixture was stirred at 23° C. for 2 h. (2-Fluorophenyl)acetonitrile (5.87 mL, 45.6 mmol) and cesium carbonate (7.42 g, 22.8 mmol) were added and the resulting mixture was stirred for 1 h. The mixture was filtered and water was added to the filtrate. The mixture was extracted with ethyl acetate (3×). The combined organic extracts were washed with water (3×), brine, dried over sodium sulfate, filtered and concentrated. Purification by silica gel chromatography (0% ethyl acetate→50% ethyl acetate/hexane) gave the title compound as a racemic mixture of cis and trans diastereomers. MS: m/z=378.1 (M+CH$_3$CN+1).

Step B: tert-Butyl [(3S,5S)-5-(2-fluorophenyl)-2-oxopiperidin-3-yl]carbamate To a solution of methyl N-(tert-butoxycarbonyl)-4-(2-fluorophenyl)-5-nitrilonorvalinate (3.88 g, 11.5 mmol) in ethanol (50 mL) was added Raney nickel (slurry in water, ca. 10 g). The mixture was placed under a balloon of hydrogen and the reaction was stirred at 23° C. for 4 h. The mixture was filtered and concentrated to afford a mixture of 4 diastereoisomers. A solution of this residue in ethanol (100 mL) was stirred in the presence of solid potassium carbonate (1.30 g, 9.44 mmol) at 60° C. for 2 h. The bulk of the ethanol was removed under reduced pressure and the remaining slurry was diluted with water to afford a white precipitate. The precipitate was filtered, washed with water and then dried under vacuum at 40° C. for 18 h. The enantiomers were separated using normal-phase HPLC using a ChiralPak® AD column, eluting with 40% hexane in ethanol (0.1% diethylamine used as a modifier) to afford the title compound as the second major enantiomer to elute. MS: m/z=331.1 (M+Na).

Step C: tert-Butyl [(3S,5S)-5-(2-fluorophenyl)-1-(2-methylpropyl)-2-oxopiperidin-3-yl]carbamate To a pre-cooled 0° C. solution of tert-butyl [(3S,5S)-5-(2-fluorophenyl)-2-oxopiperidin-3-yl]carbamate (0.85 g, 2.76 mmol) in tetrahydrofuran:N-methyl-2-pyrrolidinone (2:1, 18 mL) was added lithium bis(trimethylsilyl)amide (3.58 mL, 3.58 mmol, 1 M in THF) and the mixture was stirred at 0° C. for 30 min. 1-Iodo-2-methylpropane (0.48 mL, 4.13 mmol) was added and the resulting mixture was stirred at 0° C. for 2 h and then warmed to 23° C. and stirred for an additional 18 h. The mixture was diluted with water and extracted with ethyl acetate (3×). The combined organic extracts were washed with water, brine, dried over sodium sulfate, filtered and concentrated. Purification by silica gel chromatography (0% ethyl acetate→70% ethyl acetate/hexane) was followed by separation of the cis/trans diastereomers using supercritical fluid chromatography with a ChiralPak® AD column and eluting with 20% ethanol in carbon dioxide to afford the title compound as the second diastereomer to elute. MS: m/z=387.2 (M+Na).

Step D: (3S,5S)-3-Amino-5-(2-fluorophenyl)-1-(2-methylpropyl)piperidin-2-one A solution of tert-butyl [(3S,5S)-5-(2-fluorophenyl)-1-(2-methylpropyl)-2-oxopiperidin-3-yl]carbamate (150 mg, 0.41 mmol) in ethyl acetate (20 mL), pre-cooled to 0° C. was sparged with HCl gas for ~1 min. The ice-bath was removed and the acidic solution was allowed to warm to 23° C. as stirring was continued for 2 h. The mixture was then concentrated to dryness to afford the title compound as a hydrochloride salt. MS: m/z=265.1 (M+1).

INTERMEDIATE 8

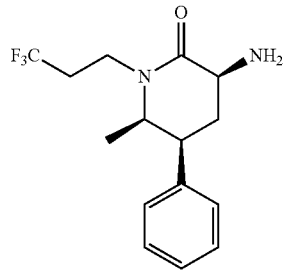 [SMILES: C[C@@H]1[C@H](c2ccccc2)C[C@H](N)C(=O)N1CCC(F)(F)F]

(3S,5S,6R)-3-Amino-6-methyl-5-phenyl-1-(3,3,3-trifluoropropyl)piperidin-2-one

Step A: Methyl 2-[(tert-butoxycarbonyl)amino]-4-(3-chlorophenyl)-5-oxohexanoate A mixture of cesium carbonate (9.80 g, 30.1 mmol) and methyl N-(tert-butoxycarbonyl)-3-iodo-D-alaninate (9.90 g, 30.1 mmol) in DMF (75 mL) was stirred at 23° C. for 45 min before 1-(3-chlorophenyl)propan-2-one (6.09 g, 36.1 mmol) and additional cesium carbonate (9.80 g, 30.1 mmol) were added. The resulting mixture was stirred for 2.5 h. The majority of the DMF was then removed under reduced pressure at a bath temperature of <40° C. The concentrated mixture was partitioned between water (100 mL) and ethyl acetate (2×200 mL). The combined organic layers were washed with brine, dried over sodium sulfate and concentrated to give the title compound as a 1:1 racemic mixture of cis and trans diastereomers, which was used without further purification. MS: m/z=392.1 (M+Na).

Step B: tert-Butyl [(3S,5S,6R)-6-methyl-2-oxo-5-phenyl-1-(3,3,3-trifluoropropyl)piperidin-3-yl]carbamate To a mixture of racemic cis and trans methyl 2-[(tert-butoxycarbonyl)amino]-4-(3-chlorophenyl)-5-oxohexanoate (1.80 g, 4.87 mmol) in DCE (24 mL) were added glacial acetic acid (1.39 mL, 24.3 mmol), 3,3,3-trifluoropropylamine (1.10 g, 9.73 mmol) and 4 Å molecular sieves (500 mg). The mixture was stirred at 23° C. for 20 min and then sodium triacetoxyborohydride (3.09 g, 14.6 mmol) was added. The mixture was stirred at 23° C. for 18 h. The mixture was diluted with water and extracted with ethyl acetate (3×). Molecular sieves were removed by filtration and the combined organic extracts were washed with water, brine, dried over sodium sulfate, filtered and concentrated. Purification by silica gel chromatography (5% ethyl acetate→100% ethyl acetate/hexane) afforded a mixture of six isomers. To this mixture of isomers was added 10 wt. % palladium on carbon (315 mg, 0.294 mmol) in ethanol (100 mL) was stirred under a balloon of hydrogen at 23° C. for 16 h. The catalyst was removed by filtration through Celite® and washed thoroughly with ethanol and ethyl acetate. Purification of the residue by reverse phase chromatography (C-18, 5% acetonitrile→95% acetonitrile/water) with 0.1% trifluoroacetic acid followed by separation of the isomers using supercritical fluid chromatography with a ChiralPak® IC column and eluting with 10% methanol and 5% acetonitrile in 85% carbon dioxide to afford the title compound as the seventh isomer to elute. MS: m/z=423.2 (M+Na).

Step C: (3S,5S,6R)-3-Amino-6-methyl-5-phenyl-1-(3,3,3-trifluoropropyl)piperidin-2-one A solution of tert-butyl [(3S,5S,6R)-6-methyl-2-oxo-5-phenyl-1-(3,3,3-trifluoropropyl)piperidin-3-yl]carbamate (152 mg, 0.380 mmol) in ethyl acetate (10 mL), pre-cooled to 0° C. was sparged with HCl gas for ~1 min. The ice-bath was removed and the acidic solution was allowed to warm to 23° C. as stirring was continued for 2 h. The mixture was then concentrated to dryness to afford the title compound as a hydrochloride salt. MS: m/z=301.3 (M+1).

INTERMEDIATE 9

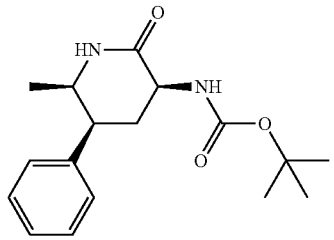 [SMILES: C[C@H]1NC(=O)[C@@H](NC(=O)OC(C)(C)C)C[C@H]1c1ccccc1]

tert-Butyl [(3S,5S,6R)-6-methyl-2-oxo-5-phenylpiperidin-3-yl]carbamate

Step A: Methyl 2-[(tert-butoxycarbonyl)amino]-4-(4-chlorophenyl)-5-oxohexanoate To a solution of methyl N-(tert-butoxycarbonyl)-3-iodo-L-alaninate (215 g, 652 mmol) and 4-chlorophenylacetone (100 g, 593 mmol) in N,N-dimethylformamide (1.5 L) was added cesium carbonate (483 g, 1.48 mol) at room temperature. After 4 h, the mixture was then added to a stirring solution of pH 7 buffer and EtOAc. The aqueous layer was extracted with EtOAc and the combined organics were washed with pH 7 buffer, dried over sodium sulfate, filtered and concentrated. The crude product was purified by silica gel chromatography (10% ethyl acetate/heptane→30% ethyl acetate/heptane) to provide the title compound as a mixture of diastereomers. MS: m/z=392.1 (M+Na).

Step B: tert-Butyl [5-(4-chlorophenyl)-6-methyl-2-oxopiperidin-3-yl]carbamate To a solution of methyl 2-[(tert-butoxycarbonyl)amino]-4-(4-chlorophenyl)-5-oxohexanoate (21.6 g, 58.4 mmol) in methanol (200 mL) were added ammonium acetate (45.0 g, 584 mmol), acetic acid (50.2 mL, 876 mmol), and sodium cyanoborohydride (5.51 g, 87.7 mmol). The mixture was heated at 60° C. for a total of 4 h. The mixture was then allowed to cool to ambient temperature and sodium bicarbonate and water were added. The mixture was extracted with ethyl acetate (3×). The combined organic extracts were washed with brine, dried over magnesium sulfate, filtered and concentrated. Ethanol (240 mL) and potassium carbonate (40.4 g, 292 mmol) were added. The mixture was stirred 1.5 h at 60° C. to effect epimerization to the desired epimer. Water was added followed by extraction with ethyl acetate (3×). The combined organic extracts were washed with brine, dried over magnesium sulfate, filtered and concentrated. Purification by silica gel chromatography (100% dichloromethane→90% dichloromethane/methanol with 0.1% ammonium hydroxide) gave the title compound as a mixture of isomers. MS: m/z=361.2 (M+Na).

Step C: tert-Butyl [(3S,5S,6R)-6-methyl-2-oxo-5-phenylpiperidin-3-yl]carbamate To a solution of tert-butyl [5-(4-chlorophenyl)-6-methyl-2-oxopiperidin-3-yl]carbamate (12.1 g, 35.7 mmol) in methanol (179 mL) was added 10% palladium on activated carbon (7.6 g, 7.1 mmol). The resulting mixture stirred 6.5 h under 1 atmosphere of hydrogen. The mixture was filtered and concentrated. Ethanol (180 mL), triethylamine (4.98 mL, 35.7 mmol) and 10% palladium on activated carbon (7.6 g, 7.1 mmol) added. The mixture was stirred 2 h 15 min under hydrogen atmosphere at a pressure of 50 psi and then was filtered and concentrated. Dichloromethane (350 mL), triethylamine (2.49 mL, 17.9 mmol), and di-tert-butyl dicarbonate (2.07 mL, 8.93 mmol) were added, and the mixture was stirred for 30 min. Saturated aqueous sodium bicarbonate was added and the mixture was extracted with dichloromethane (2×). The combined organic extracts were washed with brine, dried over magnesium sulfate, filtered and concentrated. Purification by silica gel chromatography (100% dichloromethane→90% dichloromethane/methanol with 0.1% ammonium hydroxide) gave the title compound as a mixture of isomers. The mixture was purified by HPLC (Chiral Pak® AD column, 60% ethanol/hexanes with 0.1% diethylamine). Purification by reverse chromatography (C-18, 90% water/acetonitrile→5% water/acetonitrile with 0.1% trifluoroacetic acid) gave the title compound. MS: m/z=327.3 (M+Na).

INTERMEDIATE 10

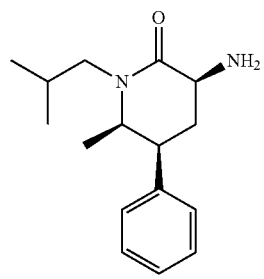 [SMILES: CC(C)CN1C(=O)[C@@H](N)C[C@@H](c2ccccc2)[C@H]1C]

(3S,5S,6R)-3-Amino-6-methyl-1-(2-methylpropyl)-5-phenylpiperidin-2-one

Step A: tert-Butyl [(3S,5S,6R)-6-methyl-1-(2-methylprop-2-en-1-yl)-2-oxo-5-phenylpiperidin-3-yl]carbamate To a pre-cooled 0° C. solution of tert-butyl [(3S,5S,6R)-6-methyl-2-oxo-5-phenylpiperidin-3-yl]carbamate (described in Intermediate 9, step C, 0.20 g, 0.657 mmol) in tetrahydrofuran:N-methyl-2-pyrrolidinone (2:1, 4.0 mL) was added lithium bis(trimethylsilyl)amide (0.735 mL, 0.735 mmol, 1 M in THF) and the mixture was stirred at 0° C. for 10 min. 3-Bromo-2-methylpropene (0.31 mL, 3.29 mmol) and sodium iodide (0.098 g, 0.66 mmol) were added and the resulting mixture was stirred at 0° C. for 2 h and then warmed to 23° C. and stirred for an additional 18 h. The mixture was diluted with water and extracted with ethyl acetate (3×). The combined organic extracts were washed with water, brine, dried over sodium sulfate, filtered and concentrated. Purification by silica gel chromatography (20% ethyl acetate→80% ethyl acetate/hexane) afforded the title compound. MS: m/z=381.3 (M+Na).

Step B: tert-Butyl [(3S,5S,6R)-6-methyl-1-(2-methylpropyl)-2-oxo-5-phenylpiperidin-3-yl]carbamate To a solution of tert-butyl [(3S,5S,6R)-6-methyl-1-(2-methylprop-2-en-1-yl)-2-oxo-5-phenylpiperidin-3-yl]carbamate (0.129 g, 0.364 mmol) in ethanol (15 mL) was added 10 wt. % palladium on carbon (39 mg, 0.036 mmol) and the mixture was stirred under a balloon of hydrogen at 23° C. for 1 h. The catalyst was removed by filtration through Celite® and washed thoroughly with ethanol and ethyl acetate. Concentration of the organics afforded the title compound which was used as is. MS: m/z=361.2 (M+1).

Step C: (3S,5S,6R)-3-Amino-6-methyl-1-(2-methylpropyl)-5-phenylpiperidin-2-one A solution of tert-butyl [(3S,5S,6R)-6-methyl-1-(2-methylpropyl)-2-oxo-5-phenylpiperidin-3-yl]carbamate (140 mg, 0.39 mmol) in ethyl acetate (10 mL), pre-cooled to 0° C. was sparged with HCl gas for ~1 min. The ice-bath was removed and the acidic solution was allowed to warm to 23° C. as stirring was continued for 2 h. The mixture was then concentrated to dryness to afford the title compound as a hydrochloride salt. MS: m/z=261.3 (M+1).

INTERMEDIATE 11

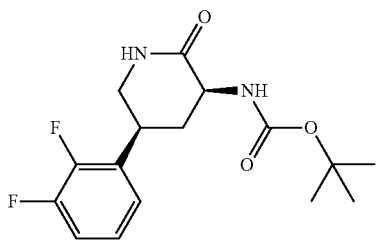 [SMILES: CC(C)(C)OC(=O)N[C@H]1C[C@@H](c2cccc(F)c2F)CNC1=O]

tert-Butyl [(3S,5S)-5-(2,3-difluorophenyl)-2-oxopiperidin-3-yl]carbamate

Step A: Methyl 2-[(tert-butoxycarbonyl)amino]-4-cyano-4-(2,3-difluorophenyl)butanoate To a solution of (2,3-difluorophenyl)acetonitrile (18.6 g, 122 mmol) in N,N-dimethylformamide (243 mL) at 0° C. was added sodium hydride (60% dispersion in mineral oil) (4.37 g, 109 mmol). After 20 min, methyl N-(tert-butoxycarbonyl)-3-iodo-D-alaninate (20.0 g, 60.8 mmol) was added, and the resulting mixture stirred 50 min. Saturated aqueous sodium bicarbonate was added, and the mixture was warmed to ambient temperature. Water was added and the mixture was extracted with ethyl acetate (3×). The combined organic extracts were washed with water (3×), brine, dried over magnesium sulfate, filtered and concentrated. Purification by silica gel chromatography (100% hexanes→20% hexanes/ethyl acetate) gave the title compound. MS: m/z=377.3 (M+Na).

Step B: tert-Butyl [(3S,5S)-5-(2,3-difluorophenyl)-2-oxopiperidin-3-yl]carbamate To a solution of methyl 2-[(tert-butoxycarbonyl)amino]-4-cyano-4-(2,3-difluorophenyl)butanoate (11.0 g, 31.0 mmol) in methanol (621 mL) was added palladium hydroxide on carbon powder (20% palladium, with moisture ca 60%) (5.45 g, 3.10 mmol). The mixture was pressurized to 50 psi under an atmosphere of hydrogen. After 90 min, the mixture was filtered and concentrated. Purification by chromatography (Chiral Pak® AD® column, 60% ethanol/hexanes with 0.1% diethylamine) gave the title compound. MS: m/z=349.3 (M+Na). $^1$H NMR (500 MHz, CDCl$_3$): δ 7.11-6.96 (m, 3H); 5.87 (s, 1H); 5.47 (s, 1H); 4.22-4.16 (m, 1H); 3.63-3.52 (m, 2H); 3.38 (t, J=11.2 Hz, 1H); 2.70 (s, 1H); 2.09 (q, J=12.3 Hz, 1H); 1.45 (s, 9H).

INTERMEDIATE 12

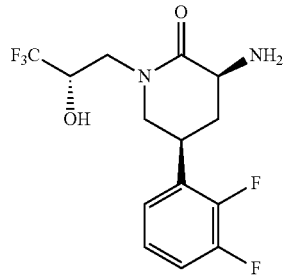 [SMILES: N[C@H]1C[C@@H](c2cccc(F)c2F)CN(C[C@H](O)C(F)(F)F)C1=O]

(3S,5S)-3-Amino-5-(2,3-difluorophenyl)-1-[(2S)-3,3,3-trifluoro-2-hydroxypropyl]piperidin-2-one

Step A: tert-Butyl {(3S,5S)-5-(2,3-difluorophenyl)-2-oxo-1-[(2S)-3,3,3-trifluoro-2-hydroxypropyl]piperidin-3-yl}carbamate To a pre-cooled −30° C. solution of tert-butyl [(3S,5S)-5-(2,3-difluorophenyl)-2-oxopiperidin-3-yl]carbamate (described in Intermediate 11, step B, 56 mg, 0.172 mmol) in tetrahydrofuran:N-methyl-2-pyrrolidinone (2:1, 0.8 mL) was added lithium bis(trimethylsilyl)amide (0.22 mL, 0.22 mmol, 1 M in THF) and the mixture was stirred at −30° C. for 30 min. (2S)-2-(Trifluoromethyl)oxirane (19 mg, 0.172 mmol) was added and the resulting mixture was stirred at −30° C. for 2 h. The mixture was diluted with water and extracted with ethyl acetate (3×). The combined organic extracts were washed with water, brine, dried over sodium sulfate, filtered and concentrated. Purification by silica gel chromatography (0% ethyl acetate→90% ethyl acetate/hexane) afforded the title compound. MS: m/z=461.2 (M+Na).

Step B: (3S,5S)-3-Amino-5-(2,3-difluorophenyl)-1-[(2S)-3,3,3-trifluoro-2-hydroxypropyl]piperidin-2-one A solution of tert-butyl {(3S,5S)-5-(2,3-difluorophenyl)-2-oxo-1-[(2S)-3,3,3-trifluoro-2-hydroxypropyl]piperidin-3-yl}carbamate (39 mg, 0.089 mmol) in ethyl acetate (5 mL), pre-cooled to 0° C. was sparged with HCl gas for ~1 min. The ice-bath was removed and the acidic solution was allowed to warm to 23° C. as stirring was continued for 2 h. The mixture was then concentrated to dryness to afford the title compound as a hydrochloride salt. MS: m/z=339.1 (M+1).

INTERMEDIATE 13

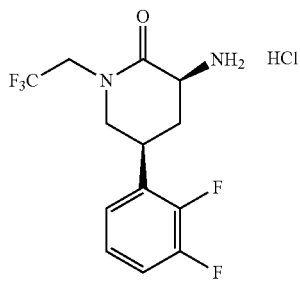 [SMILES: N[C@H]1C[C@@H](c2cccc(F)c2F)CN(CC(F)(F)F)C1=O ; Cl]

(3S,5S)-3-Amino-5-(2,3-difluorophenyl)-1-(2,2,2-trifluoroethyl)piperidin-2-one hydrochloride Step A: Ethyl 4-cyano-4-(2,3-difluorophenyl)butanoate To a mixture of (2,3-difluorophenyl)acetonitrile (40.5 g, 265 mmol), ethyl acrylate (24 mL, 220 mmol), and hydroquinone (50 mg, 0.45 mmol) was added KOH (2 M in MeOH, 2.0 mL, 4.0 mmol) and the resulting mixture was heated at 160° C. for 16 h and then allowed to cool to ambient temperature. The crude mixture was purified by silica gel chromatography, eluting with a gradient of hexanes:EtOAc—100:0 to 50:50, to give the title compound. MS: m/z=207.9 (M−OEt).

Step B: 5-(2,3-Difluorophenyl)piperidin-2-one

A mixture of ethyl 4-cyano-4-(2,3-difluorophenyl)butanoate (18.5 g, 73.1 mmol), Raney nickel (slurry in water, ca. 30 g), and ammonia (2.0 M in EtOH, 550 mL) was stirred vigorously under an atmosphere of hydrogen (ca. 1 atm) for 18 h. The reaction mixture was filtered through a pad of Celite®, washing with EtOH, and the filtrate was concentrated in vacuo to give a crude solid. Recrystallization from EtOAc afforded the title compound. MS: m/z=211.9 (M+1).

Step C: 5-(2,3-Difluorophenyl)-1-(2,2,2-trifluoroethyl)piperidin-2-one

To a stirred solution of 5-(2,3-difluorophenyl)piperidin-2-one (8.88 g, 42 mmol) in THF (250 mL) and NMP (170 mL) at 0° C. was added lithium bis(trimethylsilyl)amide (1.0 M in THF, 48 mL, 48 mmol) over 5 min, keeping the internal temperature of the reaction mixture below 5° C. The resulting mixture was stirred at 0° C. for 15 min, then 2,2,2-trifluoroethyl triflate (11.2 g, 48 mmol) was added dropwise, keeping the internal temperature of the reaction mixture below 5° C. The reaction mixture was allowed to warm slowly to ambient temperature and stirring was continued for 3 h. The resulting mixture was partitioned between saturated aqueous sodium bicarbonate (800 mL) and EtOAc (1 L). The organic layer was removed and the aqueous phase was extracted further with EtOAc (500 mL). The combined organic extracts were washed with water, then brine, then dried over sodium sulfate, filtered, and concentrated to dryness in vacuo. The crude product was purified by silica gel chromatography, eluting with a gradient of hexanes:EtOAc—100:0 to 0:100, to give the title compound. MS: m/z=293.9 (M+1).

Step D: (3R,5R & 3S,5S)-3-Azido-5-(2,3-difluorophenyl)-1-(2,2,2-trifluoroethyl)piperidin-2-one To a stirred solution of lithium bis(trimethylsilyl)amide (1.0 M in THF, 26.3 mL, 26.3 mmol) in THF (120 mL) at −78° C. was added a cold (−78° C.) solution of 5-(2,3-difluorophenyl)-1-(2,2,2-trifluoroethyl)piperidin-2-one (6.42 g, 21.9 mmol) in THF (100 mL) dropwise, keeping the internal temperature of the reaction mixture below −65° C. The resulting mixture was stirred at −78° C. for 30 min, then a cold (−78° C.) solution of 2,4,6-triisopropylbenzenesulfonyl azide (Harmon et al. (1973) J. Org. Chem. 38, 11-16) (8.81 g, 28.5 mmol) in THF (80 mL) was added dropwise, keeping the internal temperature of the reaction mixture below −65° C. The reaction mixture was stirred at −78° C. for 45 min, then AcOH (6.0 mL, 105 mmol) was added. The resulting mixture was allowed to warm slowly to ambient temperature and was partitioned between saturated aqueous sodium bicarbonate (1 L) and CH₂Cl₂ (1.5 L). The organic layer was washed with brine, then dried over sodium sulfate, filtered, and concentrated to dryness in vacuo. The crude product was purified by silica gel chromatography, eluting with a gradient of hexanes:EtOAc—100:0 to 40:60, to give the title compound. MS: m/z=334.9 (M+1).

Step E: tert-Butyl [(3S,5S)-5-(2,3-difluorophenyl)-2-oxo-1-(2,2,2-trifluoroethyl)piperidin-3-yl]carbamate To a mixture of (3R,5R & 3S,5S)-3-azido-5-(2,3-difluorophenyl)-1-(2,2,2-trifluoroethyl)piperidin-2-one (6.14 g, 18.4 mmol) and di-tert-butyl dicarbonate (4.81 g, 22.0 mmol) in EtOH (160 mL) was added 10% palladium on carbon (0.98 g, 0.92 mmol) and the resulting mixture was stirred vigorously under an atmosphere of hydrogen (ca. 1 atm) for 18 h. The reaction mixture was filtered through a pad of Celite®, washing with EtOH, and the filtrate was concentrated in vacuo to give a crude solid. The crude product was purified by silica gel chromatography, eluting with a gradient of CH₂Cl₂:EtOAc—100:0 to 60:40, to give the racemic product. Separation of the enantiomers was achieved by HPLC on a Chiralcel® AD column, eluting with EtOH:hexanes:Et₂NH—60:40:0.04, to give tert-butyl [(3R,5R)-5-(2,3-difluorophenyl)-2-oxo-1-(2,2,2-trifluoroethyl)piperidin-3-yl]carbamate as the first major peak, and tert-butyl [(3S,5S)-5-(2,3-difluorophenyl)-2-oxo-1-(2,2,2-trifluoroethyl)piperidin-3-yl]carbamate, the title compound, as the second major peak. MS: m/z=431.0 (M+Na).

Step F: (3S,5S)-3-Amino-5-(2,3-difluorophenyl)-1-(2,2,2-trifluoroethyl)piperidin-2-one hydrochloride A solution of tert-butyl [(3S,5S)-5-(2,3-difluorophenyl)-2-oxo-1-(2,2,2-trifluoroethyl)piperidin-3-yl]carbamate (1.50 g, 3.67 mmol) in EtOAc (30 mL) at 0° C. was saturated with HCl(g) and aged for 30 min. The resulting mixture was concentrated in vacuo to give the title compound. MS: m/z=309.0 (M+1); $^1$H NMR (500 MHz, CD$_3$OD) δ 7.29-7.17 (m, 3H), 4.36-4.25 (m, 2H), 4.12 (dq, 1H, J=15.1, 9.3 Hz), 3.84 (m, 1H), 3.75 (ddd, 1H, J=12.0, 5.4, 1.7 Hz), 3.64 (t, 1H, J=11.6 Hz), 2.46 (m, 1H), 2.37 (q, 1H, J=12.2 Hz).

INTERMEDIATE 14

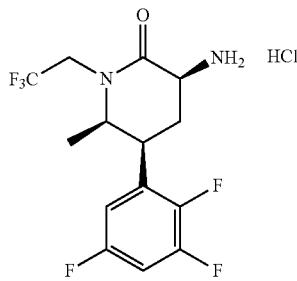 [SMILES: C[C@@H]1[C@H](c2cc(F)cc(F)c2F)C[C@H](N)C(=O)N1CC(F)(F)F ; Cl]

(3S,5S,6R)-3-Amino-6-methyl-1-(2,2,2-trifluoroethyl)-5-(2,3,5-trifluorophenyl)piperidin-2-one hydrochloride Step A: 5-Bromo-6-methyl-1-(2,2,2-trifluoroethyl)pyridin-2(1H)-one To a stirred mixture of 3-bromo-6-hydroxy-2-methylpyridine (25.0 g, 133 mmol) and cesium carbonate (52.0 g, 160 mmol) in 1,4-dioxane (600 mL) was added 2,2,2-trifluoroethyl triflate (40.1 g, 173 mmol) and the resulting mixture was heated at 50° C. for 4 h and then allowed to cool to ambient temperature. The resulting mixture was filtered and the filtrate was concentrated to dryness in vacuo. The crude product was purified by silica gel chromatography, eluting with a gradient of CH$_2$Cl$_2$:EtOAc—100:0 to 60:40, to give the title compound. MS: m/z=269.9 (M+1).

Step B: 6-Methyl-1-(2,2,2-trifluoroethyl)-5-(2,3,5-trifluorophenyl)pyridin-2(1H)-one Argon was bubbled through a stirred solution of 5-bromo-6-methyl-1-(2,2,2-trifluoroethyl)pyridin-2(1H)-one (9.43 g, 34.9 mmol) in THF (280 mL) for 15 min. To this solution were added 2,3,5-trifluorophenylboronic acid (12.3 g, 69.8 mmol), then cesium fluoride (10.6 g, 69.8 mmol), and finally bis(tri-tert-butylphosphine)palladium(0) (892 mg, 1.75 mmol), and argon was bubbled through the mixture for 5 min after each addition. The reaction mixture was stirred at ambient temperature for 90 min and was then partitioned between saturated aqueous sodium bicarbonate (500 mL) and EtOAc (600 mL). The organic layer was removed and the aqueous phase was extracted further with EtOAc (300 mL). The combined organic extracts were washed with brine, then dried over sodium sulfate, filtered, and concentrated to dryness in vacuo. The crude product was purified by silica gel chromatography, eluting with a gradient of hexanes:EtOAc—100:0 to 0:100, to give the title compound. MS: m/z=322.0 (M+1).

Step C: (5S,6R & 5R,6S)-6-Methyl-1-(2,2,2-trifluoroethyl)-5-(2,3,5-trifluorophenyl)piperidin-2-one A mixture of 6-methyl-1-(2,2,2-trifluoroethyl)-5-(2,3,5-trifluorophenyl)pyridin-2(1H)-one (3.73 g, 11.6 mmol) and platinum(IV) oxide (659 mg, 2.90 mmol) in MeOH (200 mL) was shaken on a Parr hydrogenation apparatus under an atmosphere of hydrogen (ca. 45 psi) for 2 h. The reaction mixture was filtered through a pad of Celite®, washing with MeOH, and the filtrate was concentrated in vacuo to give a crude solid. The crude product was purified by silica gel chromatography, eluting with a gradient of hexanes:Et$_2$O—100:0 to 0:100, to give the title compound. MS: m/z=326.0 (M+1).

Step D: (5S,6R & 5R,6S)-3-Azido-6-methyl-1-(2,2,2-trifluoroethyl)-5-(2,3,5-trifluorophenyl)piperidin-2-one To a stirred solution of lithium bis(trimethylsilyl)amide (1.0 M in THF, 36 mL, 36 mmol) in THF (180 mL) at −78° C. was added a cold (−78° C.) solution of (5S,6R & 5R,6S)-6-methyl-1-(2,2,2-trifluoroethyl)-5-(2,3,5-trifluorophenyl)piperidin-2-one (9.68 g, 29.8 mmol) in THF (100+20 mL) dropwise, keeping the internal temperature of the reaction mixture below −65° C. The resulting mixture was stirred at −78° C. for 30 min, then a cold (−78° C.) solution of 2,4,6-triisopropylbenzenesulfonyl azide (Harmon et al. (1973) *J. Org. Chem.* 38, 11-16) (11.97 g, 38.7 mmol) in THF (100 mL) was added dropwise, keeping the internal temperature of the reaction mixture below −65° C. The reaction mixture was stirred at −78° C. for 45 min, then AcOH (7.8 mL, 140 mmol) was added. The resulting mixture was allowed to warm slowly to ambient temperature and was poured into saturated aqueous sodium bicarbonate (750 mL) and the mixture was extracted with CH$_2$Cl$_2$ (2×750 mL). The combined organic layers were washed with brine, then dried over sodium sulfate, filtered, and concentrated to dryness in vacuo. The crude product was purified by silica gel chromatography, eluting with a gradient of hexanes:Et$_2$O—100:0 to 0:100, to give the title compound. MS: m/z=367.1 (M+1).

Step E: tert-Butyl [(5S,6R & 5R,6S)-6-methyl-2-oxo-1-(2,2,2-trifluoroethyl)-5-(2,3,5-trifluorophenyl)piperidin-3-yl]carbamate To a mixture of (5S,6R & 5R,6S)-3-azido-6-methyl-1-(2,2,2-trifluoroethyl)-5-(2,3,5-trifluorophenyl)piperidin-2-one (1.80 g, 4.91 mmol) and di-tert-butyl dicarbonate (1.18 g, 5.41 mmol) in EtOH (30 mL) was added 10% palladium on carbon (200 mg, 0.19 mmol) and the resulting mixture was stirred vigorously under an atmosphere of hydrogen (ca. 1 atm) for 1 h. The reaction mixture was filtered through a pad of Celite®, washing with EtOH, and the filtrate was concentrated in vacuo to give a crude solid. The crude product was purified by silica gel chromatography, eluting with a gradient of hexanes:EtOAc—100:0 to 30:70, to give the title compound. MS: m/z=463.2 (M+Na).

Step F: tert-Butyl [(3S,5S,6R)-6-methyl-2-oxo-1-(2,2,2-trifluoroethyl)-5-(2,3,5-trifluorophenyl)piperidin-3-yl]carbamate To a stirred solution of tert-butyl [(5S,6R & 5R,6S)-6-methyl-2-oxo-1-(2,2,2-trifluoroethyl)-5-(2,3,5-trifluorophenyl)piperidin-3-yl]carbamate (4.90 g, 11.1 mmol) in EtOH (100 mL) was added potassium carbonate (3.84 g, 27.8 mmol) and the resulting mixture was heated at 50° C. for 2 h. The reaction mixture was allowed to cool to ambient temperature and concentrated in vacuo to a volume of ca. 30 mL.

The concentrated mixture was poured into saturated aqueous sodium bicarbonate (75 mL) and the mixture was extracted with EtOAc (2×125 mL). The combined organic layers were dried over sodium sulfate, filtered, and concentrated to dryness in vacuo. The crude product was purified by silica gel chromatography, eluting with a gradient of hexanes:EtOAc—100:0 to 0:100, to give the racemic product. Separation of the enantiomers was achieved by HPLC on a Chiralcel® AD column, eluting with EtOH:hexanes:Et$_2$NH—80:20:0.02, to give tert-butyl [(3R,5R,6S)-6-methyl-2-oxo-1-(2,2,2-trifluoroethyl)-5-(2,3,5-trifluorophenyl)piperidin-3-yl]carbamate as the first major peak, and tert-butyl [(3S,5S,6R)-6-methyl-2-oxo-1-(2,2,2-trifluoroethyl)-5-(2,3,5-trifluorophenyl)piperidin-3-yl]carbamate, the title compound, as the second major peak. MS: m/z=463.2 (M+Na).

Step G: (3S,5S,6R)-3-Amino-6-methyl-1-(2,2,2-trifluoroethyl)-5-(2,3,5-trifluorophenyl)piperidin-2-one hydrochloride A solution of tert-butyl [(3S,5S,6R)-6-methyl-2-oxo-1-(2,2,2-trifluoroethyl)-5-(2,3,5-trifluorophenyl)piperidin-3-yl]carbamate (402 mg, 0.913 mmol) in EtOAc (10 mL) was saturated with HCl(g) and aged for 30 min. The resulting mixture was concentrated in vacuo to give the title compound. MS: m/z=341.0 (M+1); $^1$H NMR (500 MHz, CD$_3$OD) δ 7.20 (m, 1H), 6.94 (m, 1H), 4.78 (dq, 1H, J=15.4, 9.3 Hz), 4.26 (dd, 1H, J=12.1, 6.7 Hz), 4.08-4.00 (m, 2H), 3.73 (dq, 1H, J=15.4, 8.8 Hz), 2.57 (q, 1H, J=12.5 Hz), 2.36 (ddd, 1H, J=12.5, 6.6, 2.0 Hz), 1.07 (d, 3H, J=6.6 Hz).

INTERMEDIATE 15

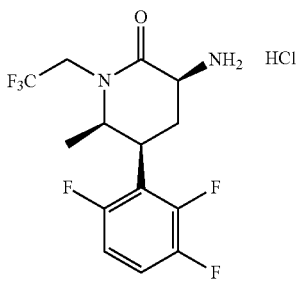 [SMILES: C[C@@H]1[C@H](c2c(F)ccc(F)c2F)C[C@H](N)C(=O)N1CC(F)(F)F ; Cl]

(3S,5S,6R)-3-Amino-6-methyl-1-(2,2,2-trifluoroethyl)-5-(2,3,6-trifluorophenyl)piperidin-2-one hydrochloride Step A: (5S,6R & 5R,6S)-6-Methyl-1-(2,2,2-trifluoroethyl)-5-(2,3,6-trifluorophenyl)piperidin-2-one Essentially following the procedures described in Intermediate 14, but using 2,3,6-trifluorophenylboronic acid in place of 2,3,5-trifluorophenylboronic acid, the title compound was obtained. MS: m/z=326.0 (M+1).

Step B: (3S,5S,6R & 3R,5R,6S)-3-Azido-6-methyl-1-(2,2,2-trifluoroethyl)-5-(2,3,6-trifluorophenyl)piperidin-2-one To a stirred solution of lithium bis(trimethylsilyl)amide (1.0 M in THF, 4.80 mL, 4.80 mmol) in THF (20 mL) at −78° C. was added a cold (−78° C.) solution of (5S,6R & 5R,6S)-6-methyl-1-(2,2,2-trifluoroethyl)-5-(2,3,6-trifluorophenyl)piperidin-2-one (1.30 g, 4.00 mmol) in THF (10 mL) dropwise, keeping the internal temperature of the reaction mixture below −65° C. The resulting mixture was stirred at −78° C. for 30 min, then a cold (−78° C.) solution of 2,4,6-triisopropyl-benzenesulfonyl azide (Harmon et al. (1973) J. Org. Chem. 38, 11-16) (1.61 g, 5.20 mmol) in THF (10 mL) was added dropwise, keeping the internal temperature of the reaction mixture below −65° C. The reaction mixture was stirred at −78° C. for 30 min, then AcOH (1.05 mL, 18.4 mmol) was added. The resulting mixture was allowed to warm slowly to ambient temperature and was poured into saturated aqueous sodium bicarbonate (50 mL) and the mixture was extracted with EtOAc (2×75 mL). The combined organic layers were washed with brine, then dried over sodium sulfate, filtered, and concentrated to dryness in vacuo. The crude product was purified by silica gel chromatography, eluting with a gradient of hexanes:EtOAc—100:0 to 20:80, to give the diastereomeric azide products (3R,5S,6R & 3S,5R,6S)-3-azido-6-methyl-1-(2,2,2-trifluoroethyl)-5-(2,3,5-trifluorophenyl)piperidin-2-one, which eluted second, and the title compound, which eluted first. MS: m/z=367.1 (M+1).

Step C: tert-Butyl [(3S,5S,6R)-6-methyl-2-oxo-1-(2,2,2-trifluoroethyl)-5-(2,3,6-trifluorophenyl)piperidin-3-yl]carbamate To a solution of (3S,5S,6R & 3R,5R,6S)-3-azido-6-methyl-1-(2,2,2-trifluoroethyl)-5-(2,3,5-trifluorophenyl)piperidin-2-one (280 mg, 0.764 mmol) and di-tert-butyl dicarbonate (217 mg, 0.994 mmol) in EtOH (5 mL) was added 10% palladium on carbon (25 mg, 0.024 mmol) and the resulting mixture was stirred vigorously under an atmosphere of hydrogen (ca. 1 atm) for 1 h. The reaction mixture was filtered through a pad of Celite®, washing with EtOH, and the filtrate was concentrated in vacuo to give a crude solid. The crude product was purified by silica gel chromatography, eluting with a gradient of hexanes:EtOAc—100:0 to 30:70, to give the racemic title compound. Separation of the enantiomers was achieved by SFC on a ChiralTech IC column, eluting with CO$_2$:MeOH:CH$_3$CN—90:6.6:3.3, to give tert-butyl [(3R,5R,6S)-6-methyl-2-oxo-1-(2,2,2-trifluoroethyl)-5-(2,3,6-trifluorophenyl)piperidin-3-yl]carbamate as the first major peak, and tert-butyl [(3S,5S,6R)-6-methyl-2-oxo-1-(2,2,2-trifluoroethyl)-5-(2,3,6-trifluorophenyl)piperidin-3-yl]carbamate, the title compound, as the second major peak. MS: m/z=463.2 (M+Na).

Step D: (3S,5S,6R)-3-Amino-6-methyl-1-(2,2,2-trifluoroethyl)-5-(2,3,6-trifluorophenyl)piperidin-2-one hydrochloride A solution of tert-butyl [(3S,5S,6R)-6-methyl-2-oxo-1-(2,2,2-trifluoroethyl)-5-(2,3,6-trifluorophenyl)piperidin-3-yl]carbamate (122 mg, 0.277 mmol) in EtOAc (10 mL) was saturated with HCl(g) and aged for 30 min. The resulting mixture was concentrated in vacuo to give the title compound. MS: m/z=341.1 (M+1); $^1$H NMR (500 MHz, CD$_3$OD) δ 7.33 (qd, 1H, J=9.3, 4.9 Hz), 7.05 (tdd, 1H, J=9.8, 3.7, 2.2 Hz), 4.78 (dq, 1H, J=15.4, 9.3 Hz), 4.22 (dd, 1H, J=12.2, 6.6 Hz), 4.06 (ddd, 1H, J=13.3, 4.5, 2.7 Hz), 3.97 (m, 1H), 3.73 (dq, 1H, J=15.4, 8.8 Hz), 2.91 (qt, 1H, J=12.7, 3.1 Hz), 2.36 (ddd, 1H, J=12.7, 6.4, 2.0 Hz), 1.22 (d, 3H, J=6.6 Hz).

The intermediates appearing in the following tables were prepared by analogy to the above intermediates, as described or prepared as a result of similar transformations with modifications known to those skilled in the art. The requisite starting materials were described herein, commercially available, known in the literature, or readily synthesized by one skilled in the art. Straightforward protecting group strategies were applied in some routes. In some cases, relevant experimental procedures are indicated in the tables.

TABLE 1

| Intermediate | R² | Ar | MS (M + 1) | Relevant procedures |
|---|---|---|---|---|
| 16 | H | 2,3,5-trifluorophenyl | 327.0 | Int. 13 |
| 17 | H | 2-chloro-6-fluorophenyl | 324.9 | Int. 13 |
| 18 | H | 2,6-dichlorophenyl | 341.0 | Int. 13 |
| 19 | H | 2,3-dichlorophenyl | 341.0 | Int. 13 |
| 20 | H | 2,3,6-trifluorophenyl | 326.9 | Int. 13 |
| 21 | Me | 2,3,5,6-tetrafluorophenyl | 359.0 | Int. 14 |
| 22 | Me | 3-fluoro-2-methylphenyl | 319.1 | Int. 14 |
| 23 | Me | 2-chlorophenyl | 321.2 | Int. 6 |
| 24 | Me | 3-methylphenyl | 301.2 | Int. 6 |

TABLE 2

| Intermediate | R¹ | Ar | MS (M + 1) | Relevant procedures |
|---|---|---|---|---|
| 25 | 2,2,2-trifluoroethyl | 2-fluorophenyl | 291.1 | Int. 7 |
| 26 | cyclobutylmethyl | 2-fluorophenyl | 277.2 | Int. 7 |
| 27 | cyclobutylmethyl | 2,3-difluorophenyl | 295.2 | Int. 7 |
| 28 | isopropyl | 2-fluorophenyl | 251.2 | Int. 7 |

TABLE 3

| Intermediate | R¹ | R² | MS (M + 1) | Relevant procedures |
|---|---|---|---|---|
| 29 | cyclopropylmethyl | methyl | 259.3 | Int. 10 |
| 30 | [1-(trifluoromethyl)cyclopropyl]methyl | methyl | 327.2 | Int. 10 |

TABLE 3-continued

| Intermediate | R¹ | R² | MS (M + 1) | Relevant procedures |
|---|---|---|---|---|
| 31 | 2,2-difluoroethyl | methyl | 269.3 | Int. 10 |
| 32 | [(1R)-2,2-difluorocyclopropyl]methyl | methyl | 295.2 | Int. 10 |
| 33 | [(1S)-2,2-difluorocyclopropyl]methyl | methyl | 295.2 | Int. 10 |

EXAMPLE 1

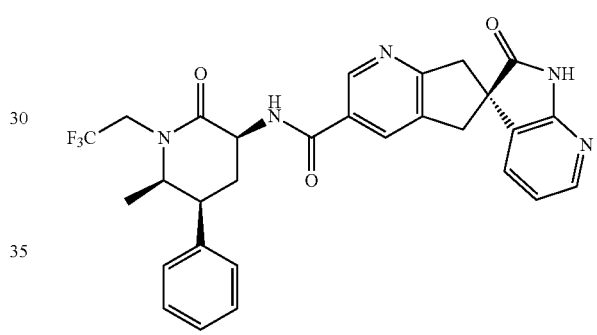

(6S)-N-[(3S,5S,6R)-6-Methyl-2-oxo-5-phenyl-1-(2,2,2-trifluoroethyl)piperidin-3-yl]-2'-oxo-1',2',5,7-tetrahydrospiro[cyclopenta[b]pyridine-6,3'-pyrrolo[2,3-b]pyridine]-3-carboxamide (Benzotriazol-1-yloxy)tris(dimethylamino)phosphonium hexafluorophosphate (1.89 g, 4.28 mmol) was added to a solution of (6S)-2'-oxo-1',2',5,7-tetrahydrospiro[cyclopenta[b]pyridine-6,3'-pyrrolo[2,3-b]pyridine]-3-carboxylic acid (described in Intermediate 1) (1.10 g, 3.92 mmol), (3S,5S,6R)-3-amino-6-methyl-5-phenyl-1-(2,2,2-trifluoroethyl)piperidin-2-one hydrochloride (described in Intermediate 4) (1.15 g, 3.56 mmol), and N,N-diisopropylethylamine (3.11 mL, 17.8 mmol) in DMF (40 mL), and the resulting mixture was stirred at 23° C. for 3 h. The reaction mixture was then partitioned between saturated aqueous sodium bicarbonate solution (200 mL) and ethyl actetate (3×200 mL). The combined organic layers were washed with brine, dried over sodium sulfate, and concentrated. The residue was purified by flash column chromatography on silica gel, eluting with hexanes initially, then grading to 100% EtOAc before stepping to 5% MeOH in EtOAc to afford the title compound as an amorphous solid, which was further purified by the following crystallization procedure. A solution of the amorphous product in a minimal amount of methanol required for dissolution was diluted with 10 volumes water, and the resulting slurry was seeded with crystalline product and stirred at 23° C. for 4 h. The solids were filtered, washed with water, and dried under a stream of nitrogen to give the title compound as a crystalline solid. HRMS: m/z=550.2068, calculated m/z=550.2061 for $C_{29}H_{27}F_3N_5O_3$. $^1H$ NMR (500 MHz, CDCl$_3$) δ 8.91 (s, 1H), 8.70 (s, 1H), 8.17 (dd, 1H, J=5.4, 1.5 Hz), 8.04 (s, 1H), 7.37 (m, 3H), 7.29 (t, 1H, J=7.3 Hz), 7.21 (d, 2H, J=7.3 Hz), 7.13 (dd, 1H, J=7.3, 1.2 Hz), 6.89 (dd, 1H, J=7.3, 5.4 Hz), 4.99-4.90 (m, 1H), 4.53 (dt, 1H, J=10.7, 6.6 Hz), 3.94 (p, 1H, J=5.9 Hz), 3.78 (d, 1H, J=17.1 Hz), 3.67 (d, 1H, J=16.4 Hz), 3.65 (m, 1H), 3.34-3.26 (m, 1H), 3.28 (d, 1H, J=17.1 Hz), 3.17 (d, 1H, J=16.6 Hz), 2.79 (m, 1H), 2.58 (q, 1H, J=12.7 Hz), 1.07 (d, 3H, J=6.6 Hz).

EXAMPLE 2

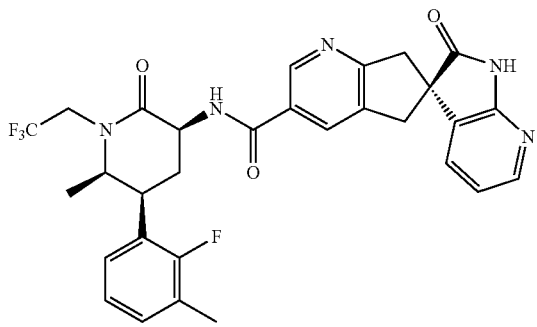 [SMILES: Cc1cccc([C@@H]2C[C@H](NC(=O)c3cnc4c(c3)C[C@@]3(C4)C(=O)Nc4ncccc43)C(=O)N(CC(F)(F)F)[C@@H]2C)c1F]

(6S)-N-[(3S,5S,6R)-5-(2-Fluoro-3-methylphenyl)-6-methyl-2-oxo-1-(2,2,2-trifluoroethyl)piperidin-3-yl]-2'-oxo-1',2',5,7-tetrahydrospiro[cyclopenta[b]pyridine-6,3'-pyrrolo[2,3-b]pyridine]-3-carboxamide (Benzotriazol-1-yloxy)tris(dimethylamino)phosphonium hexafluorophosphate (239 mg, 0.416 mmol) was added to a solution of (6S)-2'-oxo-1',2',5,7-tetrahydrospiro[cyclopenta[b]pyridine-6,3'-pyrrolo[2,3-b]pyridine]-3-carboxylic acid (described in Intermediate 1) (140 mg, 0.499 mmol), (3S,5S,6R)-3-amino-5-(2-fluoro-3-methylphenyl)-6-methyl-1-(2,2,2-trifluoroethyl)piperidin-2-one hydrochloride (described in Intermediate 5) (147 mg, 0.416 mmol), and N,N-diisopropylethylamine (0.363 mL, 2.08 mmol) in DMF (4.0 mL), and the resulting mixture was stirred at 23° C. for 16 h. The reaction mixture was purified by reverse-phase HPLC, eluting with 5% acetonitrile in water (0.1% TFA used as a modifier) initially, grading to 95% acetonitrile in water. The desired fractions were partitioned between ethyl acetate and saturated aqueous sodium bicarbonate solution. The organic layer was washed with brine, dried over sodium sulfate and concentrated to give the title compound. HRMS: m/z=582.2134, calculated m/z=582.2123 for $C_{30}H_{28}F_4N_5O_3$. $^1H$ NMR (500 MHz, CDCl$_3$) δ 8.90 (s, 1H), 8.34 (s, 1H), 8.17 (dd, 1H, J=5.4, 1.5 Hz), 8.05 (s, 1H), 7.27 (obscured m, 1H), 7.29 (t, 1H, J=7.3 Hz), 7.12 (dd, 1H, J=7.3, 1.5 Hz), 7.03 (t, 1H, J=7.8 Hz), 6.98 (t, 1H, J=6.8 Hz), 6.89 (dd, 1H, J=7.3, 5.1 Hz), 4.96-4.87 (m, 1H), 4.55 (dt, 1H, J=11.5, 5.8 Hz), 4.09 (p, 1H, J=5.8 Hz), 3.94 (dt, 1H, J=13.4, 3.2 Hz), 3.78 (d, 1H, J=17.3 Hz), 3.67 (d, 1H, J=16.4 Hz), 3.36-3.28 (m, 1H), 3.28 (d, 1H, J=17.3 Hz), 3.18 (d, 1H, J=16.4 Hz), 2.75 (m, 1H), 2.57 (q, 1H, J=12.5 Hz), 2.30 (s, 3H), 1.08 (d, 3H, J=6.6 Hz).

EXAMPLE 3

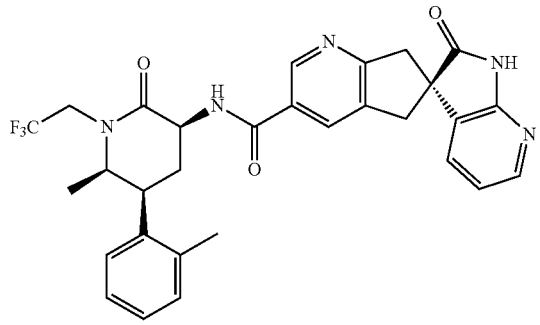 [SMILES: Cc1ccccc1[C@@H]1C[C@H](NC(=O)c2cnc3c(c2)C[C@@]2(C3)C(=O)Nc3ncccc32)C(=O)N(CC(F)(F)F)[C@@H]1C]

(6S)-N-[(3S,5S,6R)-6-Methyl-5-(2-methylphenyl)-2-oxo-1-(2,2,2-trifluoroethyl)piperidin-3-yl]-2'-oxo-1',2',5,7-tetrahydrospiro[cyclopenta[b]pyridine-6,3'-pyrrolo[2,3-b]pyridine]-3-carboxamide $N^1$-((Ethylimino)methylene)-$N^3$,$N^3$-dimethylpropane-1,3-diamine hydrochloride (0.10 g, 0.53 mmol) was added to a solution of (6S)-2'-oxo-1',2',5,7-tetrahydrospiro[cyclopenta[b]pyridine-6,3'-pyrrolo[2,3-b]pyridine]-3-carboxylic acid (described in Intermediate 1) (111 mg, 0.39 mmol), (3S,5S,6R)-3-amino-6-methyl-5-(2-methylphenyl)-1-(2,2,2-trifluoroethyl)piperidin-2-one hydrochloride (described in Intermediate 6) (127 mg, 0.38 mmol), 3H-[1,2,3]triazolo[4,5-b]pyridin-3-ol(HOAt, 15 mg, 0.11 mmol), and triethylamine (0.16 mL, 0.91 mmol) in DMF (3 mL), and the resulting mixture was stirred at 23° C. for 18 h. The reaction mixture was then partitioned between saturated aqueous sodium bicarbonate solution (10 mL) and ethyl acetate (2×30 mL). The combined organic layers were washed with brine, dried over sodium sulfate, and concentrated. The residue was purified by flash column chromatography on silica gel, eluting with 1% methanol→7% methanol/dichloromethane to afford the title compound. HRMS: m/z=564.2219 (M+1), calculated m/z=564.2234 for $C_{30}H_{28}F_3N_5O_3$. $^1H$ NMR (500 MHz, CDCl$_3$) δ 8.91 (s, 1H), 8.56 (s, 1H), 8.17 (dd, 1H, J=5.0, 1.5 Hz), 8.05 (s, 1H), 7.30 (d, 1H, J=5.0 Hz), 7.20 (m, 3H), 7.12 (m, 2H), 6.89 (dd, 1H, J=7.5, 5.0 Hz), 5.00-4.94 (m, 1H), 4.55 (m, 1H), 3.93-3.90 (m, 1H), 3.81-3.76 (m, 2H), 3.68 (d, 1H, J=16.5 Hz), 3.31-3.23 (m, 2H), 3.17 (d, 1H, J=16.5 Hz), 2.75-2.67 (m, 2H), 2.41 (s, 3H), 1.11 (d, 3H, J=6.5 Hz).

EXAMPLE 4

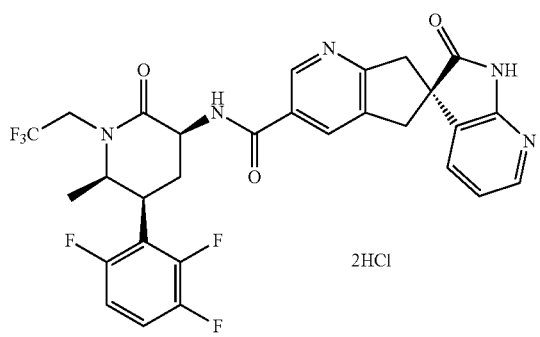 [SMILES: C[C@@H]1[C@H](c2c(F)ccc(F)c2F)C[C@H](NC(=O)c2cnc3c(c2)C[C@@]2(C3)C(=O)Nc3ncccc32)C(=O)N1CC(F)(F)F]

(6S)-N-[(3S,5S,6R)-6-Methyl-2-oxo-1-(2,2,2-trifluoroethyl)-5-(2,3,6-trifluorophenyl)piperidin-3-yl]-2'-oxo-1',2',5,7-tetrahydrospiro[cyclopenta[b]pyridine-6,3'-pyrrolo[2,3-b]pyridine]-3-carboxamide dihydrochloride To a stirred mixture of (6S)-2'-oxo-1',2',5,7-tetrahydrospiro[cyclopenta[b]pyridine-6,3'-pyrrolo[2,3-b]pyridine]-3-carboxylic acid (described in Intermediate 1) (264 mg, 0.939 mmol), (3S,5S,6R)-3-amino-6-methyl-1-(2,2,2-trifluoroethyl)-5-(2,3,6-trifluorophenyl)piperidin-2-one hydrochloride (described in Intermediate 15) (295 mg, 0.782 mmol), HOBT (144 mg, 0.939 mmol), and EDC (180 mg, 0.939 mmol) in DMF (8 mL) was added N,N-diisopropylethylamine (0.34 mL, 1.96 mmol), and the resulting mixture was stirred at ambient temperature for 3 h. The reaction mixture was then poured into saturated aqueous sodium bicarbonate (30 mL) and extracted with EtOAc (2×40 mL). The combined organic layers were washed with brine, dried over sodium sulfate, and concentrated in vacuo. The residue was purified by silica gel chromatography, eluting with a gradient of $CH_2Cl_2$:MeOH:$NH_4OH$—100:0:0 to 90:10:0.1, to give the product, which was treated with HCl in EtOAc at 0° C. to afford the title compound. HRMS: m/z=604.1783 (M+1), calculated m/z=604.1778 for $C_{29}H_{24}F_6N_5O_3$. $^1$H NMR (500 MHz, $CD_3OD$) δ 9.09 (s, 1H), 8.69 (s, 1H), 8.18 (dd, 1H, J=5.9, 1.5 Hz), 7.89 (dd, 1H, J=7.3, 1.5 Hz), 7.30 (m, 1H), 7.23 (dd, 1H, J=7.3, 5.9 Hz), 7.03 (m, 1H), 4.78 (m, 1H), 4.61 (dd, 1H, J=11.5, 6.6 Hz), 4.05 (dd, 1H, J=13.8, 2.8 Hz), 3.96 (m, 1H), 3.84 (d, 1H, J=18.6 Hz), 3.76 (d, 1H, J=18.6 Hz), 3.73 (d, 1H, J=17.3 Hz), 3.72 (m, 1H), 3.61 (d, 1H, J=17.3 Hz), 3.22 (m, 1H), 2.38 (m, 1H), 1.34 (d, 3H, J=6.6 Hz).

EXAMPLE 5

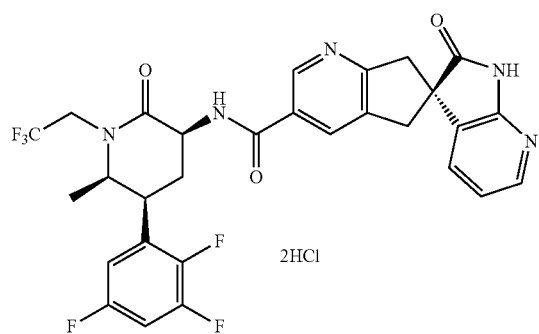 [SMILES: C[C@@H]1[C@H](c2cc(F)cc(F)c2F)C[C@H](NC(=O)c2cnc3c(c2)C[C@@]2(C3)C(=O)Nc3ncccc32)C(=O)N1CC(F)(F)F]

(6S)-N-[(3S,5S,6R)-6-Methyl-2-oxo-1-(2,2,2-trifluoroethyl)-5-(2,3,5-trifluorophenyl)piperidin-3-yl]-2'-oxo-1',2',5,7-tetrahydrospiro[cyclopenta[b]pyridine-6,3'-pyrrolo[2,3-b]pyridine]-3-carboxamide dihydrochloride Essentially following the procedures described for Example 4, but using (3S,5S,6R)-3-amino-6-methyl-1-(2,2,2-trifluoroethyl)-5-(2,3,5-trifluorophenyl)piperidin-2-one hydrochloride (described in Intermediate 14) in place of (3S,5S,6R)-3-amino-6-methyl-1-(2,2,2-trifluoroethyl)-5-(2,3,6-trifluorophenyl)piperidin-2-one hydrochloride, the title compound was obtained. HRMS: m/z=604.1778 (M+1), calculated m/z=604.1778 for $C_{29}H_{24}F_6N_5O_3$. $^1$H NMR (500 MHz, $CD_3OD$) δ 9.15 (s, 1H), 8.82 (s, 1H), 8.22 (dd, 1H, J=6.1, 1.2 Hz), 8.13 (dd, 1H, J=7.3, 1.2 Hz), 7.37 (dd, 1H, J=7.3, 6.1 Hz), 7.16 (m, 1H), 6.94 (m, 1H), 4.79 (m, 1H), 4.67 (dd, 1H, J=11.5, 7.1 Hz), 4.06 (m, 1H), 4.01 (d, 1H, J=14.2 Hz), 3.90 (s, 2H), 3.79 (d, 1H, J=18.3 Hz), 3.73 (m, 1H), 3.69 (d, 1H, J=16.6 Hz), 2.89 (q, 1H, J=12.5 Hz), 2.28 (m, 1H), 1.20 (d, 3H, J=6.4 Hz).

The examples appearing in the following tables were prepared by analogy to the above examples, as described or prepared as a result of similar transformations with modifications known to those skilled in the art. The requisite starting materials were described herein, commercially available, known in the literature, or readily synthesized by one skilled in the art. Straightforward protecting group strategies were applied in some routes.

TABLE 4

| Example | R² | Ar | HRMS (M + 1) | Calculated m/z (M + 1) |
|---|---|---|---|---|
| 6 | H | 2-fluorophenyl | 554.1809 | 554.1810 |
| 7 | Me | 2-chlorophenyl | 584.1689 | 584.1671 |
| 8 | Me | 3-methylphenyl | 564.2219 | 564.2217 |
| 9 | H | 2,3-difluorophenyl | 572.1738 | 572.1716 |
| 10 | H | 2,3,5-trifluorophenyl | 590.1635 | 590.1621 |
| 11 | H | 2-chloro-6-fluorophenyl | 588.1428 | 588.1420 |
| 12 | H | 2,6-dichlorophenyl | 604.1106 | 604.1125 |
| 13 | H | 2,3-dichlorophenyl | 604.1123 | 604.1125 |
| 14 | H | 2,3,6-trifluorophenyl | 590.1621 | 590.1621 |
| 15 | Me | 2,3,5,6-tetrafluorophenyl | 622.1681 | 622.1684 |
| 16 | Me | 3-fluoro-2-methylphenyl | 582.2123 | 582.2123 |

TABLE 5

| Example | R¹ | Ar | HRMS (M + 1) | Calculated m/z (M + 1) |
|---|---|---|---|---|
| 17 | cyclobutylmethyl | 2,3-difluorophenyl | 558.2330 | 558.2311 |
| 18 | 2-methylpropyl | 2-fluorophenyl | 528.2408 | 528.2405 |
| 19 | cyclobutylmethyl | 2-fluorophenyl | 540.2400 | 540.2405 |
| 20 | isopropyl | 2-fluorophenyl | 514.2265 | 514.2249 |
| 21 | (2S)-3,3,3-trifluoro-2-hydroxypropyl | 2,3-difluorophenyl | 602.1822 | 602.1821 |

TABLE 6

| Example | R¹ | R² | HRMS (M + 1) | Calculated m/z (M + 1) |
|---|---|---|---|---|
| 22 | 3,3,3-trifluoropropyl | methyl | 564.2225 | 564.2217 |
| 23 | 2-methylpropyl | methyl | 524.2676 | 524.2666 |
| 24 | (2S)-3,3,3-trifluoro-2-hydroxypropyl | methyl | 580.2169 | 580.2166 |
| 25 | cyclopropylmethyl | methyl | 522.2503 | 522.2500 |
| 26 | [1-(trifluoromethyl)cyclopropyl]methyl | methyl | 590.2395 | 590.2374 |
| 27 | 2,2-difluoroethyl | methyl | 532.2175 | 532.2155 |
| 28 | [2,2-difluorocyclopropyl]methyl, isomer A | methyl | 558.2323 | 558.2311 |
| 29 | [2,2-difluorocyclopropyl]methyl, isomer B | methyl | 558.2315 | 558.2311 |

TABLE 7

| Example | R² | Ar | HRMS (M + 1) | Calculated m/z (M + 1) |
|---|---|---|---|---|
| 30 | Me | phenyl | 575.2023 | 575.2013 |

TABLE 8

| Example | R² | Ar | HRMS (M + 1) | Calculated m/z (M + 1) |
|---|---|---|---|---|
| 31 | Me | phenyl | 551.2016 | 551.2013 |

TABLE 9

| Example | R¹ | R² | HRMS (M + 1) | Calculated m/z (M + 1) |
|---|---|---|---|---|
| 32 | [1-(trifluoromethyl)cyclopropyl]methyl | methyl | 591.2334 | 591.2326 |

What is claimed is:

1. A compound of Formula I:

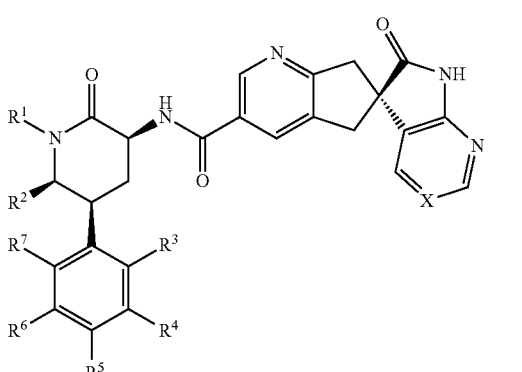

or a pharmaceutically acceptable salt thereof, wherein:
X is selected from —C($R^8$)= or —N=, wherein $R^8$ is hydrogen, F or CN;
$R^1$ is selected from the group consisting of: $C_{1-4}$alkyl, cyclopropylmethyl, cyclobutylmethyl and [1-(trifluoromethyl)cyclopropyl]methyl, each of which is optionally substituted with one or more substituents as allowed by valence independently selected from the group consisting of: F and hydroxy;
$R^2$ is selected from hydrogen and methyl;
when $R^2$ is hydrogen then
$R^3$ is selected from hydrogen, F or Cl;
$R^4$ is selected from hydrogen, F or Cl;
$R^5$ is hydrogen;
$R^6$ is selected from hydrogen or F; and
$R^7$ is selected from hydrogen, F or Cl;
except that at least two of $R^3$, $R^4$, $R^6$ and $R^7$ must be F or Cl unless $R^3$ is F in which case $R^4$, $R^6$ and $R^7$ may all be hydrogen; and if $R^4$ is Cl then $R^7$ cannot be Cl;
when $R^2$ is methyl then
$R^3$ is selected from hydrogen, methyl, F, Cl, or Br;
$R^4$ is selected from hydrogen, methyl, F or Cl;
$R^5$ is selected from hydrogen or F;
$R^6$ is selected from hydrogen or F; and
$R^7$ is selected from hydrogen, methyl, F or Cl;
except that if $R^5$ is F then at least three of $R^3$, $R^4$, $R^6$ and $R^7$ must be F; and if $R^4$ is methyl or Cl then $R^7$ cannot be methyl or Cl.

2. The compound of claim 1, or a pharmaceutically acceptable salt thereof, wherein X is —N=.

3. The compound of claim 1, or a pharmaceutically acceptable salt thereof, wherein X is —CH=.

4. The compound of claim 1, or a pharmaceutically acceptable salt thereof, wherein X is —C(CN)=.

5. The compound of claim 1, or a pharmaceutically acceptable salt thereof, wherein $R^1$ is $C_{1-4}$alkyl, optionally substituted with 1 to 3 F or hydroxy, or both.

6. The compound of claim 5, or a pharmaceutically acceptable salt thereof, wherein $R^1$ is selected from: isopropyl, 2,2,2-trifluoroethyl, 2,2-difluoroethyl, 2-methylpropyl, 3,3,3-trifluoropropyl and 3,3,3-trifluoro-2-hydroxypropyl.

7. The compound of claim 6, or a pharmaceutically acceptable salt thereof, wherein $R^1$ is 2,2,2-trifluoroethyl.

8. The compound of claim 1, or a pharmaceutically acceptable salt thereof, wherein $R^2$ is hydrogen.

9. The compound of claim 8, or a pharmaceutically acceptable salt thereof, wherein at least two of $R^3$, $R^4$, $R^6$ and $R^7$ are F or Cl, except that if $R^4$ is Cl then $R^7$ cannot be Cl.

10. The compound of claim 8, or a pharmaceutically acceptable salt thereof, wherein $R^3$ if F and $R^4$, $R^6$ and $R^7$ are hydrogen.

11. The compound of claim 1, or a pharmaceutically acceptable salt thereof, wherein $R^2$ is methyl.

12. The compound of claim 11, or a pharmaceutically acceptable salt thereof, wherein $R^5$ is F and at least three of $R^3$, $R^4$, $R^6$ and $R^7$ are F.

13. The compound of claim 11, or a pharmaceutically acceptable salt thereof, wherein $R^5$ is hydrogen and if $R^4$ is methyl or Cl then $R^7$ cannot be methyl or Cl.

14. The compound of claim 11, or a pharmaceutically acceptable salt thereof, wherein $R^3$ is selected from hydrogen, methyl, F or Cl; $R^4$ is selected from hydrogen, methyl, F or Cl; $R^5$ is hydrogen; $R^6$ is selected from hydrogen or F; and $R^7$ is selected from hydrogen, methyl, F or Cl; except that if $R^4$ is methyl or Cl then $R^7$ cannot be methyl or Cl.

15. A pharmaceutical composition which comprises an inert carrier and the compound of claim 1, or a pharmaceutically acceptable salt thereof.

16. A method of treating headache in a mammalian patient in need of such treatment, which comprises administering to the patient a therapeutically effective amount of the compound of claim 1, or a pharmaceutically acceptable salt thereof.

17. The method of claim 16, wherein the headache is migraine headache.

18. The compound

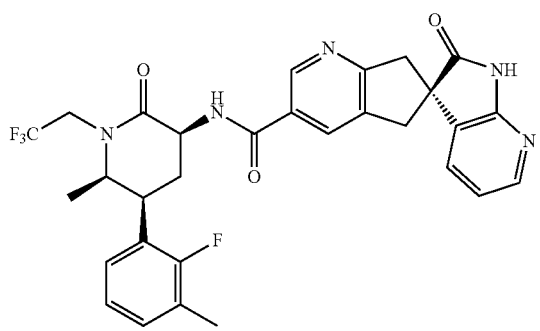 [SMILES: Cc1cccc([C@@H]2C[C@H](NC(=O)c3cnc4c(c3)C[C@@]3(C4)C(=O)Nc4ncccc43)C(=O)N(CC(F)(F)F)[C@@H]2C)c1F]

or a pharmaceutically acceptable salt thereof.

19. A pharmaceutical composition which comprises an inert carrier and the compound of claim 18, or a pharmaceutically acceptable salt thereof.

20. A method of treating migraine in a mammalian patient in need of such treatment, which comprises administering to the patient a therapeutically effective amount of the compound of claim 18, or a pharmaceutically acceptable salt thereof.

21. The compound

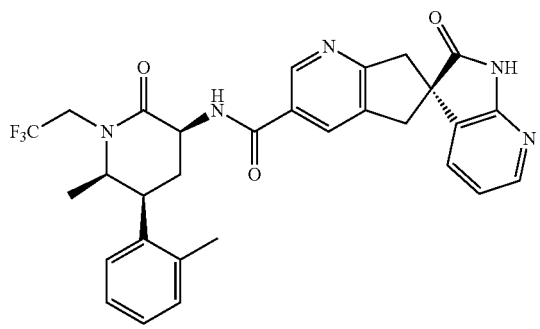 [SMILES: Cc1ccccc1[C@@H]1C[C@H](NC(=O)c2cnc3c(c2)C[C@@]2(C3)C(=O)Nc3ncccc32)C(=O)N(CC(F)(F)F)[C@@H]1C]

or a pharmaceutically acceptable salt thereof.

22. A pharmaceutical composition which comprises an inert carrier and the compound of claim 21, or a pharmaceutically acceptable salt thereof.

23. A method of treating migraine in a mammalian patient in need of such treatment, which comprises administering to the patient a therapeutically effective amount of the compound of claim 21, or a pharmaceutically acceptable salt thereof.

24. The compound

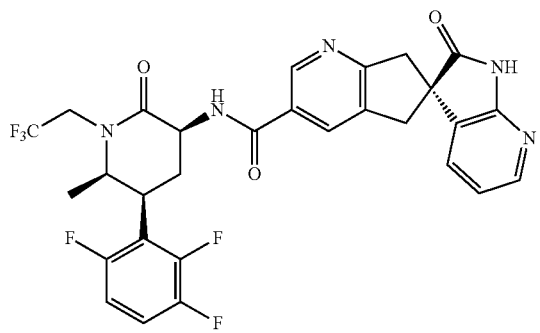 [SMILES: C[C@@H]1[C@H](c2c(F)ccc(F)c2F)C[C@H](NC(=O)c2cnc3c(c2)C[C@@]2(C3)C(=O)Nc3ncccc32)C(=O)N1CC(F)(F)F]

or a pharmaceutically acceptable salt thereof.

25. A pharmaceutical composition which comprises an inert carrier and the compound of claim 24, or a pharmaceutically acceptable salt thereof.

26. A method of treating migraine in a mammalian patient in need of such treatment, which comprises administering to the patient a therapeutically effective amount of the compound of claim 24, or a pharmaceutically acceptable salt thereof.

27. The compound

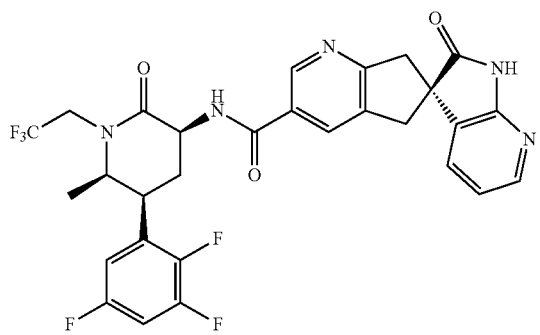 [SMILES: C[C@@H]1[C@H](c2cc(F)cc(F)c2F)C[C@H](NC(=O)c2cnc3c(c2)C[C@@]2(C3)C(=O)Nc3ncccc32)C(=O)N1CC(F)(F)F]

or a pharmaceutically acceptable salt thereof.

28. A pharmaceutical composition which comprises an inert carrier and the compound of claim 27, or a pharmaceutically acceptable salt thereof.

29. A method of treating migraine in a mammalian patient in need of such treatment, which comprises administering to the patient a therapeutically effective amount of the compound of claim 27, or a pharmaceutically acceptable salt thereof.

30. A compound selected from the following group

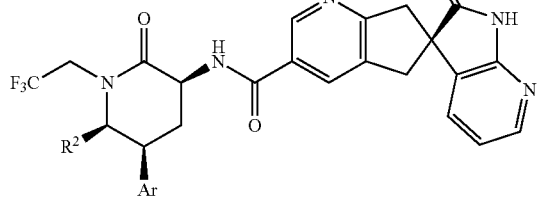

| $R^2$ | Ar |
|---|---|
| H | 2-fluorophenyl |
| Me | 2-chlorophenyl |
| Me | 3-methylphenyl |
| H | 2,3-difluorophenyl |
| H | 2,3,5-trifluorophenyl |
| H | 2-chloro-6-fluorophenyl |
| H | 2,6-dichlorophenyl |
| H | 2,3-dichlorophenyl |
| H | 2,3,6-trifluorophenyl |
| Me | 2,3,5,6-tetrafluorophenyl |
| Me | 3-fluoro-2-methylphenyl | or a pharmaceutically acceptable salt of any of the foregoing compounds.

31. A pharmaceutical composition which comprises an inert carrier and a compound of claim 30, or a pharmaceutically acceptable salt thereof.

32. A method of treating migraine in a mammalian patient in need of such treatment, which comprises administering to the patient a therapeutically effective amount of a compound of claim 30, or a pharmaceutically acceptable salt thereof.

33. A compound selected from the following group:

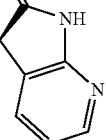

| $R^1$ | Ar |
|---|---|
| cyclobutylmethyl | 2,3-difluorophenyl |
| 2-methylpropyl | 2-fluorophenyl |
| cyclobutylmethyl | 2-fluorophenyl |
| isopropyl | 2-fluorophenyl |
| (2S)-3,3,3-trifluoro-2-hydroxypropyl | 2,3-difluorophenyl | or a pharmaceutically acceptable salt of any of the foregoing compounds.

34. A pharmaceutical composition which comprises an inert carrier and the compound of claim 33, or a pharmaceutically acceptable salt thereof.

35. A method of treating migraine in a mammalian patient in need of such treatment, which comprises administering to the patient a therapeutically effective amount of a compound of claim 33, or a pharmaceutically acceptable salt thereof.

* * * * *